(12) United States Patent
Kruck et al.

(10) Patent No.: US 12,029,808 B2
(45) Date of Patent: *Jul. 9, 2024

(54) KIT AND METHOD FOR DYEING KERATINOUS MATERIAL BY MEANS OF AMINOSILICONE AND A CHROMOPHORIC COMPOUND

(71) Applicant: Henkel AG & Co. KGaA, Duesseldorf (DE)

(72) Inventors: Constanze Kruck, Grevenbroich (DE); Melanie Moch, Dormagen (DE); Sandra Hilbig, Bochum (DE); Daniela Kessler-Becker, Leverkusen (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 166 days.

This patent is subject to a terminal disclaimer.

(21) Appl. No.: 17/762,670

(22) PCT Filed: Sep. 1, 2020

(86) PCT No.: PCT/EP2020/074358
§ 371 (c)(1),
(2) Date: Mar. 22, 2022

(87) PCT Pub. No.: WO2021/058241
PCT Pub. Date: Apr. 1, 2021

(65) Prior Publication Data
US 2022/0387292 A1  Dec. 8, 2022

(30) Foreign Application Priority Data
Sep. 23, 2019 (DE) .......................... 102019214467.5

(51) Int. Cl.
*A61Q 5/10* (2006.01)
*A61K 8/898* (2006.01)
*A61Q 5/06* (2006.01)

(52) U.S. Cl.
CPC .............. *A61K 8/898* (2013.01); *A61Q 5/065* (2013.01); *A61K 2800/43* (2013.01); *A61K 2800/882* (2013.01)

(58) Field of Classification Search
CPC ................ A61K 8/898; A61K 2800/43; A61K 2800/882; A61K 8/37; A61Q 5/065
See application file for complete search history.

(56) References Cited

U.S. PATENT DOCUMENTS

| | | | |
|---|---|---|---|
| 8,088,179 B2 * | 1/2012 | Sasao | A61K 8/891 8/581 |
| 2007/0157399 A1 * | 7/2007 | Nobuto | A61K 8/8182 8/405 |
| 2010/0083446 A1 * | 4/2010 | Brun | A61K 8/891 8/405 |
| 2016/0175210 A1 | 6/2016 | Marsh et al. | |
| 2017/0172901 A1 * | 6/2017 | Kerl | A61K 8/22 |
| 2018/0000701 A1 | 1/2018 | Schulze zur Wiesche et al. | |

FOREIGN PATENT DOCUMENTS

| | | |
|---|---|---|
| WO | 2018115059 A1 | 6/2018 |
| WO | 2020182476 A1 | 9/2020 |
| WO | 2021058157 A1 | 4/2021 |

* cited by examiner

*Primary Examiner* — Eisa B Elhilo
(74) *Attorney, Agent, or Firm* — Lorenz & Kopf, LLP

(57) ABSTRACT

The subject of the present disclosure is a process for dyeing keratinous material, in particular human hair, comprising the following steps:
(1) Providing an agent (a), wherein the agent (a) comprises:
 (a1) at least one amino-functionalized silicone polymer,
(2) Providing an agent (b), wherein the agent (b) comprises:
 (b1) Water and
 (b2) at least one fat component and
 (b3) at least one colorant compound,
(3) Preparation of an application mixture by mixing agents (a) and (b),
(4) Apply the application mixture prepared in step (3) to the keratinous material,
(5) Exposure of the application mixture applied in step (4) to the keratinous material; and
(6) Rinse the application mixture with water.

A second object of the present disclosure is a multi-component packaging unit which contains the two agents (a) and (b) in two separately assembled containers.

20 Claims, No Drawings

KIT AND METHOD FOR DYEING KERATINOUS MATERIAL BY MEANS OF AMINOSILICONE AND A CHROMOPHORIC COMPOUND

CROSS-REFERENCE TO RELATED APPLICATION

This application is a U.S. National-Stage entry under 35 U.S.C. § 371 based on International Application No. PCT/EP2020/074358, filed Sep. 1, 2020, which was published under PCT Article 21(2) and which claims priority to German Application No. 102019214467.5, filed Sep. 23, 2019, which are all hereby incorporated in their entirety by reference.

TECHNICAL FIELD

The subject of the present application is a process for dyeing keratinous material, in particular human hair, which comprises the application of at least two different agents (a) and (b). The agent (a) represents a concentrate containing at least one amino-functionalized silicone polymer (a1). The agent (b) is a carrier formulation comprising water (b1) and at least one fatty ingredient (b2) and at least one colorant compound (b3). Before application, an application mixture is prepared by mixing agents (a) and (b), which is applied to the keratin material, allowed to act and washed off again.

The second subject-matter of this application is a multi-component packaging unit (kit-of-parts) for coloring keratinous material, in particular human hair, which comprises the agents (a) and (b) separately packaged in two different containers.

BACKGROUND

Changing the shape and color of keratinous material, especially human hair, is an important area of modern cosmetics. To change the hair color, the expert knows various coloring systems depending on the coloring requirements. Oxidation dyes are usually used for permanent, intensive dyeings with good fastness properties and good grey coverage. Such colorants contain oxidation dye precursors, so-called developer components and coupler components, which, under the influence of oxidizing agents such as hydrogen peroxide, form the actual dyes among themselves. Oxidation dyes are exemplified by very long-lasting dyeing results.

When direct dyes are used, ready-made dyes diffuse from the colorant into the hair fiber. Compared to oxidative hair dyeing, the dyeings obtained with direct dyes have a shorter shelf life and quicker wash ability. Dyes with direct dyes usually remain on the hair for a period of between 5 and about 20 washes.

The use of color pigments is known for short-term color changes on the hair and/or skin. Color pigments are generally understood to be insoluble, coloring substances. These are present undissolved in the dye formulation in the form of small particles and are only deposited from the outside on the hair fibers and/or the skin surface. Therefore, they can usually be removed again without residue by a few washes with detergents containing surfactants. Various products of this type are available on the market under the name hair mascara.

The advantage of a hair mascara product is that the colorant compounds, such as pigments, are deposited only in the form of a film on the surface of the keratin fiber. The nature of the keratin fiber itself is thus not changed during the application of the product, so that the use of a hair mascara product is associated with particularly low hair damage. If the user wishes to return to his original hair color, the dye can be removed from the keratin fiber quickly, completely and without residue, without damaging the fibers or changing the original hair color. The development of pigment-based keratin colorants is therefore fully in line with the trend.

As before, however, there is still a need for optimization of this staining system, with durability and leveling capacity in particular requiring improvement.

BRIEF SUMMARY

Methods for dying keratinous material and kits-of-parts for the same are provided. in an exemplary embodiment, a method includes providing an agent (a) that includes an amino-functionalized silicone polymer (a1), and an agent (b) that includes water (b1), a fat component (b2), and a colorant compound (b3). An application mixture is prepared by mixing agents (a) and (b), and the application mixture is applied to the keratinous material. The keratinous material is exposed to the application mixture, and then the application mixture is rinsed from the keratinous material.

A kit-of-parts is provided in another embodiment. The kit-of-parts includes a first container containing an agent (a), where the agent (a) includes an amino-functionalized silicone polymer. A second container contains an agent (b), where the agent (b) includes water (b1), a fat component (b2), and a color-imparting compound (b3).

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has been the object of the present disclosure to provide a staining system having fastness properties comparable to oxidative staining, if possible. Wash fastness properties should be outstanding, but the use of oxidation dye precursors normally used for this purpose should be avoided. A technology was sought that would make it possible to fix the colorant compounds (especially pigments) known from the prior art to the hair in an extremely durable manner. When the agents are used in a dyeing process, intensive dyeing results with good fastness properties should be obtained. A particular focus of the task was to achieve a homogeneous dyeing result, i.e., the keratin fibers were to be dyed very uniformly, regardless of their structure, length and nature.

Surprisingly, it has now turned out that the above-mentioned task can be excellently solved if keratinous materials, especially hair, are dyed using a procedure in which at least two agents (a) and (b) are applied to the keratinous materials (hair). Here, the agent (a) contains at least one amino-functionalized silicone polymer (a1). The agent (a) is preferably in the form of a concentrate which can be prepared in a low-water or anhydrous form and contains the amino silicone (a1) as the main constituent. Before use, the agent (a) is mixed with a second agent (b), the agent (b) containing, in addition to water (b1), at least one fatty constituent (b2) and at least one coloring compound (b3). The application mixture prepared by mixing agents (a) and (b) is then applied to the keratin material, allowed to act and then rinsed out again with water A first object of the present disclosure is a method for coloring keratinous material, in particular human hair, comprising the following steps:
(1) Providing an agent (a), wherein the agent (a) comprises:
   (a1) at least one amino-functionalized silicone polymer,
(2) Providing an agent (b), wherein the agent (b) comprises:
   (b1) Water and
   (b2) at least one fat component and
   (b3) at least one colorant compound,
(3) Preparation of an application mixture by mixing agents (a) and (b),
(4) Apply the application mixture prepared in step (3) to the keratinous material,
(5) Exposure of the application mixture applied in step (4) to the keratinous material; and
(6) Rinse the application mixture with water.

In the work leading to the present disclosure, it has been shown that particularly intensive, homogeneous and long-lasting color results can be obtained on the keratin material if the agent (a) is provided in the form of the concentrate described above, this concentrate (a) being mixed with the actual colorant (b) only shortly before use. Surprisingly, an application mixture obtained just before application by mixing the two agents (a) and (b), compared to an otherwise identical formulation containing all the components of the two agents (a) and (b) from the beginning, allows a much more intense, homogeneous and longer lasting color result to be obtained.

Keratinic Material

Keratinous material includes hair, skin, nails (such as fingernails and/or toenails). Wool, furs and feathers also fall under the definition of keratinous material.

Preferably, keratinous material is understood to be human hair, human skin and human nails, especially fingernails and toenails. Keratinous material is understood to be human hair.

Agent (a)

In step (1) of the method as contemplated herein, agent (a) is provided. For example, the agent (a) can be present in a packaging unit or container and in this way be made available to the user. The container can be, for example, a sachet, a bottle, a can, a jar or also another container suitable for cosmetic formulations. Since the agent (a) is preferably a concentrate of the amino silicone (a1), a container suitable for concentrates can be selected particularly preferably for packaging the agent (a).

Agent (a) is exemplified by its content of the essential constituent of the present disclosure (a1).

Amino Functionalized Silicone Polymer (a1) in the Agent (a)

As an ingredient (a1) essential to the present disclosure, the agent (a) contains at least one amino-functionalized silicone polymer. The amino-functionalized silicone polymer may alternatively be referred to as amino silicone or amodimethicone.

Silicone polymers are generally macromolecules with a molecular weight of at least about 500 g/mol, preferably at least about 1000 g/mol, more preferably at least about 2500 g/mol, particularly preferably at least about 5000 g/mol, which comprise repeating organic units.

The maximum molecular weight of the silicone polymer depends on the degree of polymerization (number of polymerized monomers) and the batch size and is also partly determined by the polymerization method. For the purposes of the present disclosure, it is preferred if the maximum molecular weight of the silicone polymer is not more than about $10^7$ g/mol, preferably not more than about $10^6$ g/mol, and particularly preferably not more than about $10^5$ g/mol.

The silicone polymers comprise many Si—O repeating units, and the Si atoms may carry organic radicals such as alkyl groups or substituted alkyl groups. Alternatively, a silicone polymer is therefore also referred to as polydimethylsiloxane.

Corresponding to the high molecular weight of silicone polymers, these are based on more than about 10 Si—O repeat units, preferably more than about 50 Si—O repeat units, and more preferably more than about 100 Si—O repeat units, most preferably more than about 500 Si—O repeat units.

An amino-functionalized silicone polymer is understood to be a functionalized silicone that carries at least one structural unit with an amino group. Preferably, the amino-functionalized silicone polymer carries multiple structural units, each having at least one amino group. An amino group is understood to mean a primary amino group, a secondary amino group and a tertiary amino group. All these amino groups can be protonated in the acidic environment and are then present in their cationic form.

In principle, good effects could be obtained with amino-functionalized silicone polymers (a1) if they carry at least one primary, at least one secondary and/or at least one tertiary amino group. However, intense colorations with the best wash fastness were obtained when an amino-functionalized silicone polymer (a1) was used in agent (a), which contains at least one secondary amino group.

In a very particularly preferred embodiment, a process as contemplated herein is exemplified in that the agent (a) comprises at least one amino-functionalized silicone polymer (a1) having at least one secondary amino group.

The secondary amino group(s) may be located at various positions on the amino-functionalized silicone polymer. Particularly good effects were found when an amino-functionalized silicone polymer (a1) was used that has at least one, preferably several, structural units of the formula (Si amino).

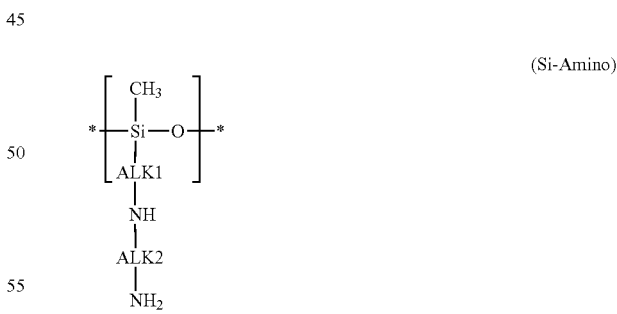

(Si-Amino)

In the structural units of the formula (Si amino), the abbreviations ALK1 and ALK2 independently stand for a linear or branched, bivalent $C_1$-$C_{20}$ alkylene group.

In another very particularly preferred embodiment, a process as contemplated herein is exemplified in that the agent (a) comprises at least one amino-functionalized silicone polymer (a1) comprising at least one structural unit of the formula (Si amino),

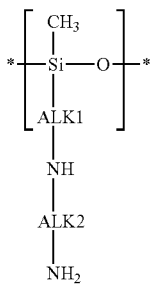

(Si-Amino)

where
ALK1 and ALK2 independently represent a linear or branched $C_1$-$C_{20}$ divalent alkylene group.

The positions marked with an asterisk (*) indicate the bond to further structural units of the silicone polymer. For example, the silicon atom adjacent to the star may be bonded to another oxygen atom, and the oxygen atom adjacent to the star may be bonded to another silicon atom or even to a $C_1$-$C_6$ alkyl group.

A bivalent $C_1$-$C_{20}$ alkylene group can alternatively be referred to as a divalent or divalent $C_1$-$C_{20}$ alkylene group, by which is meant that each ALK1 or AK2 grouping can form two bonds.

In the case of ALK1, one bond occurs from the silicon atom to the ALK1 grouping, and the second bond is between ALK1 and the secondary amino group.

In the case of ALK2, one bond is from the secondary amino group to the ALK2 grouping, and the second bond is between ALK2 and the primary amino group.

Examples of a linear bivalent $C_1$-$C_{20}$ alkylene group include the methylene group (—$CH_2$—), the ethylene group (—$CH_2$—$CH_2$—), the propylene group (—$CH_2$—$CH_2$—$CH_2$—), and the butylene group (—$CH_2$—$CH_2$—$CH_2$—$CH_2$—). The propylene group (—$CH_2$—$CH_2$—$CH_2$—) is particularly preferred. From a chain length of 3 C atoms, bivalent alkylene groups can also be branched. Examples of branched divalent, bivalent $C_3$-$C_{20}$ alkylene groups are (—$CH_2$—$CH(CH_3)$—) and (—$CH_2$—$CH(CH_3)$—$CH_2$—).

In another particularly preferred embodiment, the structural units of the formula (Si amino) represent repeat units in the amino-functionalized silicone polymer (a1), such that the silicone polymer comprises multiple structural units of the formula (Si amino).

Particularly well-suited amino-functionalized silicone polymers (a1) with at least one secondary amino group are listed below.

Dyeings with the very best wash fastnesses could be obtained if in the process as contemplated herein at least one agent (a) was applied to the keratinous material which contains at least one amino-functionalized silicone polymer (a1) comprising structural units of the formula (Si—I) and of the formula (Si-II)

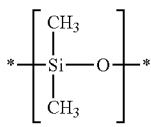

(Si-I)

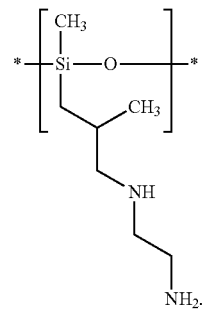

(Si-II)

In a further explicitly quite particularly preferred embodiment, a process as contemplated herein is exemplified in that the agent (a) contains at least one amino-functionalized silicone polymer (a1) which comprises structural units of the formula (Si—I) and of the formula (Si-II)

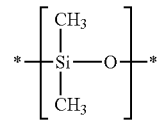

(Si-I)

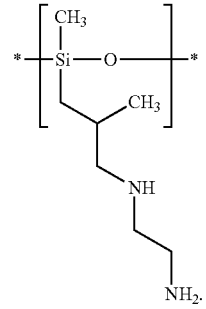

(Si-II)

A corresponding amino functionalized silicone polymer with the structural units (Si—I) and (Si-II) is, for example, the commercial product DC 2-8566 or Dowsil® 2-8566 Amino Fluid, which is commercially distributed by the Dow® Chemical Company and bears the designation "Siloxanes and Silicones, 3-[(2-aminoethyl)amino]-2-methylpropyl Me, Di-Me-Siloxane" and the CAS number 106842-44-8. Another particularly preferred commercial product is Dowsil® AP-8658 Amino Fluid, which is also sold commercially by the Dow® Chemical Company.

In the context of a further preferred embodiment, a process as contemplated herein is exemplified by the application of an agent (a) to the keratinous material, the agent (a) comprising at least one amino-functional silicone polymer (a1) of the formula of formula (Si-III),

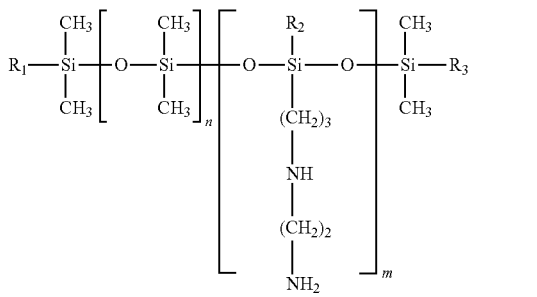

(Si-III)

where
- m and n are numbers chosen so that the sum (n+m) is in the range 1 to about 1000,
- n is a number in the range 0 to about 999 and m is a number in the range 1 to about 1000,
- R1, R2 and R3, which are the same or different, denote a hydroxy group or a C1-4 alkoxy group,
- wherein at least one of R1 to R3 represents a hydroxy group.

Further methods preferred as contemplated herein are exemplified by the application of an agent (a) to the keratinous material, the agent (a) comprising at least amino-functional silicone polymer (a1) of the formula of formula (Si-IV),

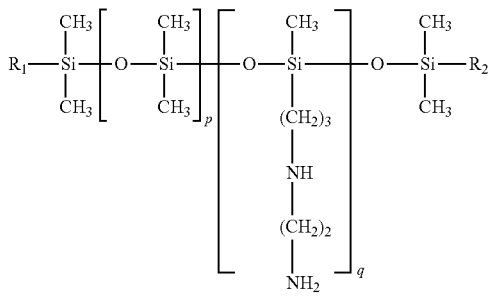

(Si-IV)

where
- p and q are numbers chosen so that the sum (p+q) is in the range 1 to about 1000,
- p is a number in the range 0 to about 999 and q is a number in the range 1 to about 1000,
- R1 and R2, which are different, denote a hydroxy group or a C1-4 alkoxy group, at least one of R1 to R2 denoting a hydroxy group.

The silicones of the formulas (Si-III) and (Si-IV) differ in the grouping at the Si atom, which carries the nitrogen-containing group: In formula (Si-III), R2 represents a hydroxy group or a C1-4 alkoxy group, while the residue in formula (Si-IV) is a methyl group. The individual Si groupings, which are marked with the indices m and n or p and q, do not have to be present as blocks; rather, the individual units can also be present in a statistically distributed manner, i.e., in the formulas (Si-III) and (Si-IV), not every R1-Si(CH$_3$)$_2$ group is necessarily bonded to an [O—Si(CH$_3$)$_2$] grouping.

Processes as contemplated herein in which an agent (a) containing at least one amino-functional silicone polymer (a1) of the formula (Si-V) is applied to the keratin fibers have also proved to be particularly effective with respect to the desired effects.

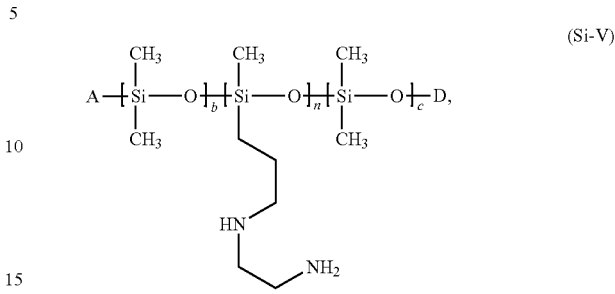

(Si-V)

where
A represents a group —OH, —O—Si(CH$_3$)$_3$, —O—Si(CH$_3$)$_2$OH, —O—Si(CH$_3$)$_2$OCH$_3$,
D represents a group —H, —Si(CH$_3$)$_3$, —Si(CH$_3$)$_2$OH, —Si(CH$_3$)$_2$OCH$_3$,
b, n and c stand for integers between 0 and about 1000, with the specifications
n>0 and b+c>0
at least one of the conditions A=-OH or D=—H is fulfilled.

In the above formula (Si-V), the individual siloxane units are statistically distributed with the indices b, c and n, i.e., they do not necessarily have to be block copolymers.

Agent (a) may further comprise one or more different amino-functionalized silicone polymers represented by the formula (Si-VI)

$$M(R_aQ_bSiO_{(4-a-b)/2})_x(R_cSiO_{(4-c)/2})_yM \quad \text{(Si-VI)}$$

in which formula above R is a hydrocarbon or a hydrocarbon radical having from 1 to about 6 carbon atoms, Q is a polar radical of the general formula —R$^1$HZ wherein R$^1$ is a divalent linking group bonded to hydrogen and the radical Z composed of carbon and hydrogen atoms, carbon, hydrogen and oxygen atoms, or carbon, hydrogen and nitrogen atoms, and Z is an organic amino functional radical containing at least one amino functional group; "a" takes values ranging from about 0 to about 2, "b" takes values ranging from about 1 to about 3, "a"+"b" is less than or equal to 3, and "c" is a number ranging from about 1 to about 3, and x is a number ranging from 1 to about 2,000, preferably from about 3 to about 50 and most preferably from about 3 to about 25, and y is a number in the range of from about 20 to about 10,000, preferably from about 125 to about 10,000 and most preferably from about 150 to about 1,000, and M is a suitable silicone end group as known in the prior art, preferably trimethylsiloxy. Non-limiting examples of radicals represented by R include alkyl radicals, such as methyl, ethyl, propyl, isopropyl, isopropyl, butyl, isobutyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halohydrocarbon radicals, such as 3-chloropropyl, 4-bromobutyl, 3,3,3-trifluoropropyl, chlorocyclohexyl, bromophenyl, chlorophenyl and the like, and sulfur-containing radicals, such as mercaptoethyl, mercaptopropyl, mercaptohexyl, mercaptophenyl and the like; preferably R is an alkyl radical containing from 1 to about 6 carbon atoms, and most preferably R is methyl. Examples of R$^1$ include methylene, ethylene, propylene, hexamethylene, decamethylene, —CH₂CH(CH₃)CH₂—, phenylene, naphthylene, —CH₂CH₂SCH₂CH₂—, —CH₂CH₂OCH₂—, —OCH₂CH₂—, —OCH₂CH₂CH₂—, —CH₂CH(CH₃)C(O)OCH₂—, —(CH₂)₃CC(O)OCH₂CH₂—, —C₆H₄C₆H₄—, —C₆H₄CH₂C₆H₄—; and —(CH₂)₃C(O)SCH₂CH₂—.

Z is an organic amino functional residue containing at least one amino functional group. One possible formula for Z is NH(CH₂)ᵤNH₂, where z is 1 or more. Another possible formula for Z is —NH(CH₂)ᵤ(CH 2)ᵤᵤNH, wherein both z and zz are independently 1 or more, this structure comprising diamino ring structures, such as piperazinyl. Z is most preferably an —NHCH₂CH₂NH₂ residue. Another possible formula for Z is —N(CH₂)ᵤ(CH₂)ᵤᵤNX₂ or —NX₂, wherein each X of X2 is independently selected from the group of hydrogen and alkyl groups having 1 to about 12 carbon atoms, and zz is 0.

Q is most preferably a polar, amine-functional radical of the formula —CH₂CH₂CH₂NHCH₂CH₂NH₂. In the formulas, "a" takes values ranging from about 0 to about 2, "b" takes values ranging from about 2 to about 3, "a"+"b" is less than or equal to 3, and "c" is a number ranging from about 1 to about 3. The molar ratio of RₐQ_b SiO_{(4-a-b)/2} units to R_c SiO_{(4-c)/2} units is in the range of about 1:2 to about 1:65, preferably from about 1:5 to about 1:65 and most preferably by about 1:15 to about 1:20. If one or more silicones of the above formula are used, then the various variable substituents in the above formula may be different for the various silicone components present in the silicone mixture.

In a particularly preferred embodiment, a method as contemplated herein is exemplified by the application of an agent (a) to the keratinous material, wherein the agent (a) contains an amino-functional silicone polymer of formula (Si-VII)

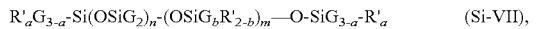   (Si-VII), wherein:
G is —H, a phenyl group, —OH, —O—CH₃, —CH₃, —O—CH₂CH₃, —CH₂CH₃, —O—CH₂CH₂CH₃, —CH₂CH₂CH₃, —O—CH(CH₃)₂, —CH(CH₃)₂, —O—CH₂CH₂CH₂CH₃, —CH₂CH₂CH₂CH₃, —O—CH₂CH(CH₃)₂, —CH₂CH(CH₃)₂, —O—CH(CH₃)CH₂CH₃, —CH(CH₃)CH₂CH₃, —O—C(CH₃)₃, —C(CH₃)₃;

a stands for a number between 0 and about 3, especially 0;

b stands for a number between 0 and about 1, especially 1, m and n are numbers whose sum (m+n) is between 1 and about 2000, preferably between about 50 and about 150, where n preferably assumes values from 0 to about 1999 and from about 49 to about 149 and m preferably assumes values from 1 to about 2000, from 1 to about 10, R' is a monovalent radical selected from
-Q-N(R")—CH₂—CH₂—N(R")₂
-Q-N(R")₂
-Q-N⁺(R")₃A⁻
-Q-N⁺H(R")₂A⁻
-Q-N⁺H₂(R")A⁻
-Q-N(R")—CH₂—CH₂—N⁺R"H₂A⁻, where each Q is a chemical bond, —CH₂—, —CH₂—CH₂—, —CH₂CH₂CH₂—, —C(CH₃)₂—, —CH₂CH₂CH₂CH₂—, —CH₂C(CH₃)₂—, —CH(CH₃)CH₂CH₂—, R" represents identical or different radicals selected from the group of —H, -phenyl, -benzyk-CH₂—CH(CH₃)Ph, the C₁₋₂₀ alkyl radicals, preferably —CH₃, —CH₂CH₃, —CH₂CH₂CH₃, —CH(CH₃)₂, —CH₂CH₂CH₂H₃, —CH₂CH(CH₃)₂, —CH(CH₃)CH₂CH₃, —C(CH₃)₃, and A represents an anion preferably selected from chloride, bromide, iodide or methosulfate.

In the context of a further preferred embodiment, a process as contemplated herein is exemplified by the application of an agent (a) to the keratinous material, the agent (a) comprising at least one amino-functional silicone polymer (a1) of the formula (Si-VIIa),

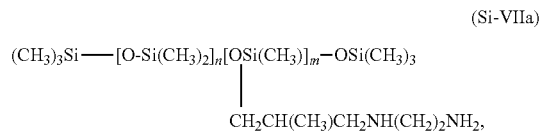

(Si-VIIa)

wherein m and n are numbers whose sum (m+n) is between 1 and about 2000, preferably between about 50 and about 150, n preferably assuming values from 0 to about 1999 and from about 49 to about 149, and m preferably assuming values from 1 to about 2000, from 1 to about 10.

According to the INCI declaration, these silicones are called trimethylsilylamodimethicones.

In another preferred embodiment, a method as contemplated herein is exemplified by the application of an agent (a) to the keratinous material, said agent (a) comprising at least one amino-functional silicone polymer of formula (Si-VIIb)

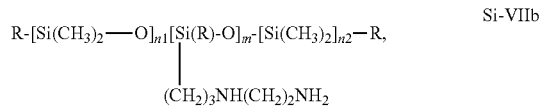

Si-VIIb in which R represents —OH, —O—CH₃ or a —CH₃ group and m, n1 and n2 are numbers whose sum (m+n1+n2) is between 1 and about 2000, preferably between about 50 and about 150, the sum (n1+n2) preferably assuming values from 0 to about 1999 and from about 49 to about 149 and m preferably assuming values from 1 to about 2000, from 1 to about 10.

According to the INCI declaration, these amino-functionalized silicone polymers are called amodimethicones.

Regardless of which amino-functional silicones are used, agents (a) as contemplated herein are preferred which contain an amino-functional silicone polymer whose amine number is above about 0.25 meq/g, preferably above about 0.3 meq/g and above about 0.4 meq/g. The amine number represents the milliequivalents of amine per gram of the amino-functional silicone. It can be determined by titration and expressed in the unit mg KOH/g.

Furthermore, agents (a) which contained a special 4-morpholinomethyl-substituted silicone polymer (a1) are also suitable for use in the process as contemplated herein. This amino-functionalized silicone polymer comprises structural units of the formulae (SI-VIII) and of the formula (Si-IX)

(Si-VIII)

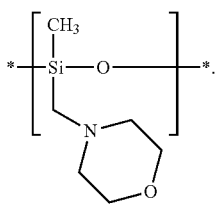
(Si-IX)

Corresponding 4-morpholinomethyl-substituted silicone polymers are described below.

A very particularly preferred amino-functionalized silicone polymer is known by the name of Amodimethicone/ Morpholinomethyl Silsesquioxane Copolymer is known and commercially available from Wacker® in the form of the raw material Belsil® ADM 8301 E.

As a 4-morpholinomethyl-substituted silicone, for example, a silicone can be used which has structural units of the formulae (Si-VIII), (Si-IX) and (Si-X)

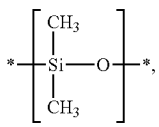
(Si-VIII)

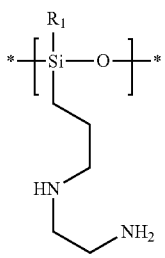
(Si-X)

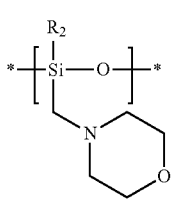
(Si-IX)

in which
R1 is —CH$_3$, —OH, —OCH$_3$, —O—CH$_2$CH$_3$, —O—CH$_2$CH$_2$CH$_3$, or —O—CH(CH$_3$)$_2$;
R2 is —CH$_3$, —OH, or —OCH$_3$.
Particularly preferred agent (a) as contemplated herein contains at least one 4-morpholinomethyl-substituted silicone of the formula (Si-XI)

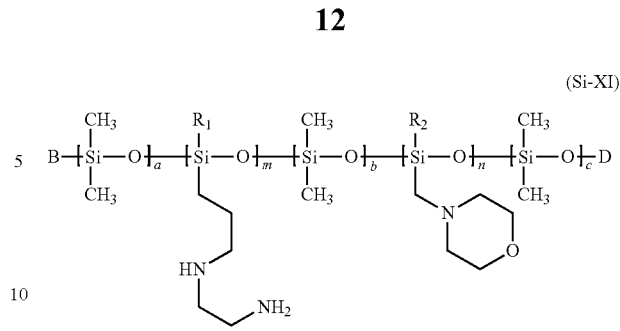
(Si-XI)

wherein
R1 is —CH$_3$, —OH, —OCH$_3$, —O—CH$_2$CH$_3$, —O—CH$_2$CH$_2$CH$_3$, or —O—CH(CH$_3$)$_2$;
R2 is —CH$_3$, —OH, or —OCH$_3$.
B represents a group —OH, —O—Si(CH$_3$)$_3$, —O—Si (CH$_3$)$_2$OH, —O—Si(CH$_3$)$_2$OCH$_3$,
D represents a group —H, —Si(CH$_3$)$_3$, —Si(CH$_3$)$_2$OH, —Si(CH$_3$)$_2$OCH$_3$, a, b and c stand independently for integers between 0 and about 1000, with the condition a+b+c>0 m and n independently of each other stand for integers between 1 and about 1000
with the proviso that
at least one of the conditions B=-OH or D=—H is fulfilled,
the units a, b, c, m and n are distributed statistically or blockwise in the molecule.
Structural formula (Si-XI) is intended to illustrate that the siloxane groups n and m do not necessarily have to be directly bonded to a terminal grouping B or D, respectively. Rather, in preferred formulas (Si-VI) a>0 or b>0 and in particularly preferred formulas (Si-VI) a>0 and c>0, i.e., the terminal grouping B or D is preferably attached to a dimethylsiloxy grouping. Also, in formula (Si-VI), the siloxane units a, b, c, m and n are preferably statistically distributed.

The silicones used as contemplated herein represented by formula (Si-VI) can be trimethylsilyl-terminated (D or B=—Si(CH$_3$)$_3$), but they can also be dimethylsilylhydroxy-terminated on two sides or dimethylsilylhydroxy-terminated and dimethylsilylmethoxy-terminated on one side. Silicones particularly preferred in the context of the present disclosure are selected from silicones in which
B=—O—Si(CH$_3$)$_2$OH and D=-Si(CH$_3$)$_3$
B=—O—Si(CH$_3$)$_2$OH and D=-Si(CH$_3$)$_2$OH
B=—O—Si(CH$_3$)$_2$OH and D=-Si(CH$_3$)$_2$OCH$_3$
B=-O—Si(CH$_3$)$_3$ and D=-Si(CH$_3$)$_2$OH
B=—O—Si(CH$_3$)$_2$OCH$_3$ and D=-Si(CH$_3$)$_2$OH
These silicones lead to exorbitant improvements in the hair properties of the hair treated with the agents of the present disclosure, and to a seriously improved protection in oxidative treatment.

The agent (a) used in the process as contemplated herein is very preferably a concentrate containing the amino-functionalized silicone polymer(s) (a1) in correspondingly high amounts. Particularly good dyeing results were obtained when the agent (a)—based on the total weight of the agent (a)—contains one or more amino-functionalized silicone polymers (a1) in a total amount of from about 5 to 100 wt. %, preferably from about 25 to 100 wt. %, more preferably from about 50 to 100 wt. % and very particularly preferably from about 75 to 100 wt. %.

In the context of this embodiment, the amino silicones (a1) are either used in substance, or a solubilizer, diluent or carrier is added in small amounts to the amino silicone(s) (a1).

In another particularly preferred embodiment, a process as contemplated herein is exemplified in that the agent (a) contains—based on the total weight of the agent (a)—one or more amino-functionalized silicone polymers (a1) in a total amount of from about 5 to 100 wt. %, preferably from about 25 to 100 wt. %, more preferably from about 50 to 100 wt. % and very particularly preferably from about 75 to 100 wt. %.

Solvent in Agent (a)

For example, a solvent may be used as the appropriate solubilizer or diluent in agent (a). For this reason, the agent (a) as contemplated herein may therefore additionally contain at least one solvent as an optional component.

Suitable solvents may include, for example, solvents selected from the group of 1,2-propylene glycol, 1,3-propylene glycol, ethylene glycol, 1,2-butylene glycol, dipropylene glycol, ethanol, isopropanol, diethylene glycol monoethyl ether, glycerol, phenoxyethanol and benzyl alcohol. The use of 1,2-propylene glycol is particularly preferred.

In another very particularly preferred embodiment, a process as contemplated herein is exemplified in that the agent (a) comprises at least one solvent selected from the group of 1,2-propylene glycol, 1,3-propylene glycol, ethylene glycol, 1,2-butylene glycol, dipropylene glycol, ethanol, isopropanol, diethylene glycol monoethyl ether, glycerol, phenoxyethanol and benzyl alcohol, very preferably 1,2-propylene glycol.

1,2-Propylene glycol is alternatively referred to as 1,2-propanediol and has CAS numbers 57-55-6 [(RS)-1,2-dihydroxypropane], 4254-14-2 [(R)-1,2-dihydroxypropane], and 4254-15-3 [(S)-1,2-dihydroxypropane]. Ethylene glycol is alternatively known as 1,2-ethanediol and carries CAS number 107-21-1. Glycerol is alternatively known as 1,2,3-propanetriol and carries CAS number 56-81-5. Phenoxyethanol has the Cas number 122-99-6.

All the solvents described previously are commercially available from various chemical suppliers, such as Aldrich® or Fluka®.

In a further preferred embodiment, a process as contemplated herein is exemplified in that the agent (a) contains—based on the total weight of the agent (a)—one or more solvents in a total amount of about 1.0 to about 80.0 wt. %, preferably about 2.0 to about 50.0 wt. %, more preferably about 3.0 to about 30.0 wt. % and very particularly preferably about 4.0 to about 20.0 wt. %.

In another very particularly preferred embodiment, a process as contemplated herein is exemplified in that the agent (a) contains—based on the total weight of the agent (a)—about 1.0 to about 95.0 wt. %, preferably about 2.0 to about 15.0 wt. %, more preferably about 3.0 to about 15.0 wt. % and very particularly preferably about 4.0 to about 10.0 wt. % of 1,2-propylene glycol.

Packaging of the Agent (a)

As described above, the agent (a) is a concentrate which preferably contains the ingredient (a1) essential to the present disclosure as its main constituent.

The work carried out in the present disclosure has led to the suggestion that the pigments used in the dyeing process and the amino-functionalized silicone polymers (a1) may interact with each other. This interaction seems to take place mainly in an aqueous environment or in an environment containing water. One assumption is that an interaction occurs between the respective surface of the pigment and the amino groups of the silicone polymer, whereby the water could possibly act as a proton donor or proton acceptor.

This assumption is supported by observations which showed that in a formulation which, in addition to amino silicone (a1) and pigment, also contained the components of the carrier formulation, i.e., water (b1) and fatty components (b2) in higher concentrations, the deposition of a resinous substance could be observed after a few days. When this formulation was used in the dyeing test after several days of storage, only dyeings with very low color intensity were obtained. Based on this observation, the confection of the amino silicones (a1) in a low-water or anhydrous environment has been found to be particularly preferable.

In a further explicitly quite particularly preferred embodiment, a process as contemplated herein is exemplified in that the agent (a) contains—based on the total weight of the agent (a)—less than about 10.0 wt. %, preferably less than about 5.0 wt. %, further preferably less than about 2.5 wt. % and very particularly preferably less than about 1.0 wt. % of water.

In other words, in a further explicitly quite particularly preferred embodiment, a process as contemplated herein is exemplified in that the agent (a)—based on the total weight of the agent (a)—has a water content of between 0 and about 10.0 wt. %, preferably between 0 and about 5.0 wt. %, more preferably between 0 and about 2.5 wt. % and very particularly preferably between 0 and about 1.0 wt. %.

Further work has now shown that, above all, the homogeneity of the color result also depends on the agent into which the colorant compounds (i.e., the pigments) are incorporated. If the pigments were stored together with the amino silicone (a1) in the form of a premix and this was mixed with a cosmetic carrier formulation only shortly before application, the color intensity and wash fastness were significantly improved. However, it has been shown that this type of packaging is also associated with some disadvantages. If the mixture of amino silicone (a1) and pigment was stored for a longer time, a reaction of the two components with each other seemed to take place due to the storage time. In low-water or anhydrous medium, this reaction was slowed down, but nevertheless became significant from storage times of several weeks. Therefore, very poor miscibility of the amino silicon/pigment mixture with the carrier material was observed during the coloration of appropriately stored agents. As a result, very inhomogeneous color results were also obtained.

For this reason, it has further been found to be particularly preferable if the agent (a) itself does not contain any pigment or if these are used only in very small amounts in the agent (a). Very small amounts of pigment can, for example, be incorporated into the agent (a) to color it or give it a more aesthetic appearance.

In a further explicitly quite particularly preferred embodiment, a process as contemplated herein is exemplified in that the agent (a) contains—based on the total weight of the agent (a)—one or more pigments in a total content of less than about 0.1 wt. %, preferably less than about 0.05 wt. % and very preferably less than about 0.01 wt. %.

In other words, in a further explicitly quite particularly preferred embodiment, a process as contemplated herein is exemplified in that the agent (a)—based on the total weight of the agent (a)—has a pigment content which is between 0 and about 0.1 wt. %, preferably between 0 and about 0.05 wt. % and very particularly preferably between 0 and about 0.01 wt. %.

It is explicitly quite preferred if the agent (a) does not contain any pigments.

Agent (b)

In step (2) of the method as contemplated herein, agent (b) is provided. For example, the agent (b) can be present in a packaging unit or container and in this way be made available to the user. The container can be, for example, a sachet, a bottle, a can, a jar or also another container suitable for cosmetic formulations.

Agent (b) represents the actual colorant and is exemplified by its content of water (b1) and fatty constituent(s) (b2) and of at least one colorant compound (b3).

When mixing the agents (a) and (b), the preferably highly concentrated and low-water concentrate (a) is mixed with the actual colorant (b). During this mixing, the amino silicones (a1) are brought into contact with the pigments (b3) and incorporated into an emulsion, so that the previously described interaction of the amino silicones (a1) and pigments (b3) only starts from this moment of mixing. Surprisingly, it was observed that this type of finishing in the dyeing process leads to color results that are intense and washfast, but in addition are also exemplified by particularly good homogeneity.

Water Content (b1) in Agent (b)

In contrast to agent (a), agent (b) preferably contains a high water content. It has been found that particularly well suited for use in the process as contemplated herein are those agent (b) which contain—based on the total weight of the agent (b)—about 50.0 to about 98.0 wt. %, preferably about 60.0 to about 90.0 wt. %, more preferably about 70.0 to about 90.0 wt. % and most preferably about 75.0 to about 90.0 wt. % of water (b1).

In a further explicitly quite particularly preferred embodiment, a process as contemplated herein is exemplified in that the agent (b) contains—based on the total weight of the agent (b)—about 50.0 to about 98.0 wt. %, preferably about 60.0 to about 90.0 wt. %, further preferably about 70.0 to about 90.0 wt. % and very particularly preferably about 75.0 to about 90.0 wt. % of water (b1).

Fat Components (b2) in the Agent (b)

A further feature of the agent (b) is its content of at least one fat constituent (b2). It has been found that the use of at least one fatty constituent results in the agent (b) being in the form of an emulsion, which allows particularly good and rapid mixing with the agent (a).

The fatty components are hydrophobic substances that can form emulsions in the presence of water, forming micelle systems.

For the purposes of the present disclosure, "fatty components" means organic compounds with a solubility in water at room temperature (22° C.) and atmospheric pressure (760 mmHg) of less than about 1 wt. %, preferably less than about 0.1 wt. %. The definition of fat constituents explicitly covers only uncharged (i.e., non-ionic) compounds. Fat components have at least one saturated or unsaturated alkyl group with at least about 12 C atoms. The molecular weight of the fat constituents is a maximum of about 5000 g/mol, preferably a maximum of about 2500 g/mol and particularly preferably a maximum of about 1000 g/mol. The fat components are neither polyoxyalkylated nor polyglycerylated compounds.

Very preferably, the fatty components (b2) contained in the agent (b) are selected from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons.

In a further preferred embodiment, a process as contemplated herein is exemplified in that the agent (b) comprises one or more fat constituents (b2) from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons.

In this context, very particularly preferred fat constituents are understood to be constituents from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons. For the purposes of the present disclosure, only non-ionic substances are explicitly regarded as fat components. Charged compounds such as fatty acids and their salts are not considered to be fat components.

The $C_{12}$-$C_{30}$ fatty alcohols can be saturated, mono- or polyunsaturated, linear or branched fatty alcohols with about 12 to about 30 C atoms.

Examples of preferred linear, saturated $C_{12}$-$C_{30}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, Cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Preferred linear unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidone alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol).

The preferred representatives for branched fatty alcohols are 2-octyl-dodecanol, 2-hexyl-dodecanol and/or 2-butyl-dodecanol.

By selecting particularly well-suited fat components, the polarity and viscosity of agent (b) can be optimally adjusted so that complete and rapid mixing is ensured when agents (a) and (b) are mixed. As a result of the high homogeneity of the application mixture prepared from (a) and (b), a particularly uniform color result can also be ensured.

In this context, it has been found that the use of at least one $C_{12}$-$C_{30}$ fatty alcohol (b2) in the agent (b) creates an optimum emulsion system.

In one embodiment, particularly good results were obtained when the agent (b) comprises one or more $C_{12}$-$C_{30}$ fatty alcohols selected from the group of dodecan-1-ol (dodecyl alcohol, lauryl alcohol), Tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol), Behenyl alcohol (docosan-1-ol), (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), Gadoleyl alcohol ((9Z)-Eicos-9-en-1-ol), Arachidone alcohol ((5Z,8Z, 11Z,14Z)-Eicosa-5,8,11,14-tetraen-1-ol), Erucyl alcohol ((13Z)-Docos-13-en-1-ol), Brassidyl alcohol ((13E)-docosen-1-ol) 2-octyl-dodecanol, 2-hexyl-dodecanol and/or 2-butyl-dodecanol.

In a further preferred embodiment, a method as contemplated herein is exemplified in that the second agent (b) comprises one or more $C_{12}$-$C_{30}$ fatty alcohols (b2) selected from the group of Dodecan-1-ol (dodecyl alcohol, lauryl alcohol),
Tetradecan-1-ol (tetradecyl alcohol, myristyl alcohol),
Hexadecan-1-ol (hexadecyl alcohol, cetyl alcohol, palmityl alcohol),
Octadecan-1-ol (octadecyl alcohol, stearyl alcohol), Arachyl alcohol (eicosan-1-ol),
Heneicosyl alcohol (heneicosan-1-ol),
Behenyl alcohol (docosan-1-ol),
(9Z)-Octadec-9-en-1-ol (oleyl alcohol),
(9E)-Octadec-9-en-1-ol (elaidyl alcohol),
(9Z,12Z)-Octadeca-9,12-dien-1-ol (linoleyl alcohol),
(9Z,12Z,15Z)-Octadeca-9,12,15-trien-1-ol (linolenoyl alcohol),
Gadoleyl alcohol ((9Z)-Eicos-9-en-1-ol),
Arachidonic alcohol ((5Z,8Z,11Z,14Z)-Eicosa-5,8,11,14-tetraen-1-ol),
Erucyl alcohol ((13Z)-docos-13-en-1-ol),
Brassidyl alcohol ((13E)-docosen-1-ol),
2-Octyl-dodecanol,
2-hexyl dodecanol and/or
2-Butyl-dodecanol.

It has been found to be particularly preferable to use one or more $C_{12}$-$C_{30}$ fatty alcohols (b2) in very specific ranges of amounts.

It is particularly preferred if the agent (b)—based on the total weight of the agent (b)—contains one or more $C_{12}$-$C_{30}$ fatty alcohols (b2) in a total amount of from about 2.0 to about 50.0 wt. %, preferably from about 3.0 to about 30.0 wt. %, more preferably from about 4.0 to about 20.0 wt. %, still more preferably from about 5.0 to about 15.0 wt. % and most preferably from about 5.0 to about 10.0 wt. %.

Furthermore, as a very particularly preferred fat component (b2), the agent (b) may also contain at least one $C_{12}$-$C_{30}$ fatty acid triglyceride, the $C_{12}$-$C_{30}$ fatty acid monoglyceride and/or $C_{12}$-$C_{30}$ fatty acid diglyceride. For the purposes of the present disclosure, a $C_{12}$-$C_{30}$ fatty acid triglyceride is understood to be the triester of the trivalent alcohol glycerol with three equivalents of fatty acid. Both structurally identical and different fatty acids within a triglyceride molecule can be involved in the formation of esters.

As contemplated herein, fatty acids are to be understood as saturated or unsaturated, unbranched or branched, unsubstituted or substituted $C_{12}$-$C_{30}$ carboxylic acids. Unsaturated fatty acids can be mono- or polyunsaturated. For an unsaturated fatty acid, its C—C double bond(s) may have the Cis or Trans configuration.

Fatty acid triglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], and/or nervonic acid [(15Z)-tetracos-15-enoic acid].

The fatty acid triglycerides can also be of natural origin. The fatty acid triglycerides or mixtures thereof occurring in soybean oil, peanut oil, olive oil, sunflower oil, macadamia nut oil, moringa oil, apricot kernel oil, marula oil and/or optionally hardened castor oil are particularly suitable for use in the product as contemplated herein.

A $C_{12}$-$C_{30}$ fatty acid monoglyceride is understood to be the monoester of the trivalent alcohol glycerol with one equivalent of fatty acid. Either the middle hydroxy group of glycerol or the terminal hydroxy group of glycerol may be esterified with the fatty acid.

$C_{12}$-$C_{30}$ fatty acid monoglycerides are particularly suitable in which a hydroxyl group of glycerol is esterified with a fatty acid, the fatty acids being selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], or nervonic acid [(15Z)-tetracos-15-enoic acid].

A $C_{12}$-$C_{30}$ fatty acid diglyceride is the diester of the trivalent alcohol glycerol with two equivalents of fatty acid. Either the middle and one terminal hydroxy group of glycerol may be esterified with two equivalents of fatty acid, or both terminal hydroxy groups of glycerol are esterified with one fatty acid each. The glycerol can be esterified with two structurally identical fatty acids or with two different fatty acids.

Fatty acid triglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], and/or nervonic acid [(15Z)-tetracos-15-enoic acid].

Particularly good results were obtained when agent (B) contained at least one $C_{12}$-$C_{30}$ fatty acid monoglyceride selected from the monoesters of glycerol with one equivalent of fatty acid selected from the group of dodecanoic acid (lauric acid), Tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), Petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid] and/or nervonic acid [(15Z)-tetracos-15-enoic acid].

In a very particularly preferred embodiment, a process as contemplated herein is exemplified in that the second agent (b) comprises at least one $C_{12}$-$C_{30}$ fatty acid monoglyceride (b2) selected from the monoesters of glycerol with one equivalent of fatty acid selected from the group of dodecanoic acid, tetradecanoic acid, hexadecanoic acid, tetracosanoic acid, octadecanoic acid, eicosanoic acid and/or docosanoic acid.

The choice of suitable amounts of $C_{12}$-$C_{30}$ fatty acid mono-, $C_{12}$-$C_{30}$ fatty acid di- and/or $C_{12}$-$C_{30}$ fatty acid triglycerides can also have a particularly strong influence on the rate of film formation originating from the $C_1$-$C_6$ alkoxy silanes. For this reason, it has proven to be particularly preferred to use one or more $C_{12}$-$C_{30}$ fatty acid mono-, $C_{12}$-$C_{30}$ fatty acid di- and/or $C_{12}$-$C_{30}$ fatty acid triglycerides (b2) in very specific ranges of amounts in the agent (b).

With regard to the solution of the problem as contemplated herein, it has proved to be particularly preferable if the agent (b)—based on the total weight of the agent (b)—contained one or more $C_{12}$-$C_{30}$ fatty acid mono-, $C_{12}$-$C_{30}$ fatty acid di- and/or $C_{12}$-$C_{30}$ fatty acid triglycerides (b2) in a total amount of about 0.1 to about 20.0 wt. %, preferably about 0.3 to about 15.0 wt. %, further preferably about 0.5 to about 10.0 wt. % and very particularly preferably about 0.8 to about 5.0 wt. %. %, preferably from about 0.3 to about 15.0 wt. %, more preferably from about 0.5 to about 10.0 wt. % and most preferably from about 0.8 to about 5.0 wt. %.

In a very particularly preferred embodiment, a process as contemplated herein is exemplified in that the agent (b) contains—based on the total weight of the agent (b)—one or more $C_{12}$-$C_{30}$ fatty acid mono-, $C_{12}$-$C_{30}$ fatty acid di- and/or $C_{12}$-$C_{30}$ fatty acid triglycerides (b2 (in a total amount of from about 0.1 to about 20.0 wt. %, preferably from about 0.3 to about 15.0 wt. %, more preferably from about 0.5 to about 10.0 wt. % and very particularly preferably from about 0.8 to about 5.0 wt. %.

The $C_{12}$-$C_{30}$ fatty acid mono-, $C_{12}$-$C_{30}$ fatty acid di- and/or $C_{12}$-$C_{30}$ fatty acid triglycerides can be used as the sole fat components (b2) in the agent (b). However, it is particularly preferred to incorporate at least one $C_{12}$-$C_{30}$ fatty acid mono-, $C_{12}$-$C_{30}$ fatty acid di- and/or $C_{12}$-$C_{30}$ fatty acid triglyceride in combination with at least one $C_{12}$-$C_{30}$ fatty alcohol into the agent (b).

Furthermore, as a very particularly preferred fatty constituent (b2), the agent (b) may also contain at least one hydrocarbon.

Hydrocarbons are compounds comprised exclusively of the atoms carbon and hydrogen with about 8 to about 80 C atoms. In this context, aliphatic hydrocarbons such as mineral oils, liquid paraffin oils (e.g., Paraffinium Liquidum or Paraffinum Perliquidum), isoparaffin oils, semi-solid paraffin oils, paraffin waxes, hard paraffin (Paraffinum Solidum), Vaseline® and polydecenes are particularly preferred.

Liquid paraffin oils (Paraffinum Liquidum and Paraffinium Perliquidum) have proven to be particularly suitable in this context. Paraffinum Liquidum, also known as white oil, is the preferred hydrocarbon. Paraffinum Liquidum is a mixture of purified, saturated, aliphatic hydrocarbons, comprised mainly of hydrocarbon chains with a C-chain distribution of about 25 to about 35 C-atoms.

Very particularly good results were obtained when the agent (b) contained at least one hydrocarbon (b2) selected from the group of mineral oils, liquid kerosene oils, isoparaffin oils, semisolid kerosene oils, kerosene waxes, hard kerosene (Paraffinum solidum), petrolatum and polydecenes.

In a very particularly preferred embodiment, a process as contemplated herein is exemplified in that the agent (b) comprises at least one fatty constituent (b2) from the group of hydrocarbons.

It has been found to be particularly preferable to use one or more hydrocarbons in very specific ranges of amounts in agent (b).

Regarding the solution of the problem as contemplated herein, it has proved to be quite particularly preferable if the agent (b)—based on the total weight of the agent (b)—contained one or more hydrocarbons (b2) in a total amount of from about 0.5 to about 20.0 wt. %, preferably from about 1.0 to about 15.0 wt. %, more preferably from about 1.5 to about 10.0 wt. % and most preferably from about 2.0 to about 8.0 wt. %.

In a very particularly preferred embodiment, a process as contemplated herein is exemplified in that the agent (b) contains—based on the total weight of the agent (b)—one or more hydrocarbons (b2) in a total amount of from about 0.5 to about 20.0 wt. %, preferably from about 1.0 to about 15.0 wt. %, more preferably from about 1.5 to about 10.0 wt. % and very particularly preferably from about 2.0 to about 8.0 wt. %.

The hydrocarbon(s) may be used as the sole fatty components (b2) in the agents (b). However, it is particularly preferred to incorporate at least one hydrocarbon in combination with at least one other constituent into the agent (b).

Very preferably, the agent contains at least one fatty constituent (b2) from the group of $C_{12}$-$C_{30}$ fatty alcohols and at least one further fatty constituent from the group of hydrocarbons.

Colorant Compound (b3) in the Agent (b)

As a third constituent essential to the present disclosure, the agent (b) used in the process as contemplated herein contains at least one color-imparting compound (b3).

For the purposes of the present disclosure, colorant compounds are substances capable of imparting a coloration to the keratin material. Particularly well-suited colorant compounds can be selected from the group of pigments, direct-acting dyes, photochromic dyes and thermochromic dyes.

In a further preferred embodiment, a process as contemplated herein is exemplified in that the agent (b) comprises at least one colorant compound (b3) from the group of pigments, direct dyes, photochromic dyes and thermochromic dyes.

Pigments within the meaning of the present disclosure are coloring compounds which have a solubility in water at 25° C. of less than 0.5 g/L, preferably less than 0.1 g/L, even more preferably less than 0.05 g/L. Water solubility can be determined, for example, by the method described below: 0.5 g of the pigment are weighed in a beaker. A stir-fish is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the possibly finely dispersed pigment, the mixture is filtered. If a proportion of undissolved pigments remains on the filter paper, the solubility of the pigment is below 0.5 g/L.

Suitable color pigments can be of inorganic and/or organic origin.

In a preferred embodiment, an agent (b) as contemplated herein is exemplified in that it contains at least one color-imparting compound (b3) from the group of inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite.

Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-containing silicates, silicates, metal sulfides, complex metal cyanides, metal sulphates, chromates and/or molybdates. Preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, CI77510) and/or carmine (cochineal).

As contemplated herein, colored pearlescent pigments are also particularly preferred color pigments. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, mainly muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

In a further preferred embodiment, a process as contemplated herein is exemplified in that the agent (b) comprises at least one colorant compound (b3) from the group of inorganic pigments, which is preferably selected from the group of colored metal oxides, metal hydroxides, metal oxide hydrates, silicates, metal sulfides, complex metal cyanides, metal sulfates, bronze pigments and/or from colored mica- or mica-based pigments coated with at least one metal oxide and/or a metal oxychloride.

In a further preferred embodiment, agent (b) used in the process as contemplated herein is exemplified in that it contains at least one coloring compound (b3) from the group of pigments selected from mica- or mica-based pigments which are reacted with one or more metal oxides from the group of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Examples of particularly suitable color pigments are commercially available under the trade names Rona®, Colorona®, Xirona®, Dichrona® and Timiron® from Merck®, Ariabel® and Unipure® from Sensient®, Prestige® from Eckart® Cosmetic Colors and Sunshine® from Sunstar®.

Particularly preferred color pigments with the trade name Colorona® are, for example:
Colorona® Copper, Merck®, MICA, CI 77491 (IRON OXIDES)
Colorona® Passion Orange, Merck®, Mica, CI 77491 (Iron Oxides), Alumina
Colorona® Patina Silver, Merck®, MICA, CI 77499 (IRON OXIDES), CI 77891 (TITANIUM DIOXIDE)
Colorona® RY, Merck®, CI 77891 (TITANIUM DIOXIDE), MICA, CI 75470 (CARMINE)
Colorona® Oriental Beige, Merck®, MICA, CI 77891 (TITANIUM DIOXIDE), CI 77491 (IRON OXIDES)
Colorona® Dark Blue, Merck®, MICA, TITANIUM DIOXIDE, FERRIC FERROCYANIDE
Colorona® Chameleon, Merck®, CI 77491 (IRON OXIDES), MICA
Colorona® Aborigine Amber, Merck®, MICA, CI 77499 (IRON OXIDES), CI 77891 (TITANIUM DIOXIDE)
Colorona® Blackstar Blue, Merck®, CI 77499 (IRON OXIDES), MICA
Colorona® Patagonian Purple, Merck®, MICA, CI 77491 (IRON OXIDES), CI 77891 (TITANIUM DIOXIDE), CI 77510 (FERRIC FERROCYANIDE)
Colorona® Red Brown, Merck®, MICA, CI 77491 (IRON OXIDES), CI 77891 (TITANIUM DIOXIDE)
Colorona® Russet, Merck®, CI 77491 (TITANIUM DIOXIDE), MICA, CI 77891 (IRON OXIDES)
Colorona® Imperial Red, Merck®, MICA, TITANIUM DIOXIDE (CI 77891), D&C RED NO. 30 (CI 73360)
Colorona® Majestic Green, Merck®, CI 77891 (TITANIUM DIOXIDE), MICA, CI 77288 (CHROMIUM OXIDE GREENS)
Colorona® Light Blue, Merck®, MICA, TITANIUM DIOXIDE (CI 77891), FERRIC FERROCYANIDE (CI 77510)
Colorona® Red Gold, Merck®, MICA, CI 77891 (TITANIUM DIOXIDE), CI 77491 (IRON OXIDES)
Colorona® Gold Plus MP 25, Merck®, MICA, TITANIUM DIOXIDE (CI 77891), IRON OXIDES (CI 77491)
Colorona® Carmine Red, Merck®, MICA, TITANIUM DIOXIDE, CARMINE
Colorona® Blackstar Green, Merck®, MICA, CI 77499 (IRON OXIDES)
Colorona® Bordeaux, Merck®, MICA, CI 77491 (IRON OXIDES)
Colorona® Bronze, Merck®, MICA, CI 77491 (IRON OXIDES)
Colorona® Bronze Fine, Merck®, MICA, CI 77491 (IRON OXIDES)
Colorona® Fine Gold MP 20, Merck®, MICA, CI 77891 (TITANIUM DIOXIDE), CI 77491 (IRON OXIDES)
Colorona® Sienna Fine, Merck®, CI 77491 (IRON OXIDES), MICA
Colorona Sienna, Merck®, MICA, CI 77491 (IRON OXIDES)
Colorona® Precious Gold, Merck®, Mica, CI 77891 (Titanium dioxide), Silica, CI 77491 (Iron oxides), Tin oxide
Colorona® Sun Gold Sparkle MP 29, Merck®, MICA, TITANIUM DIOXIDE, IRON OXIDES, MICA, CI 77891, CI 77491 (EU)
Colorona® Mica Black, Merck®, CI 77499 (Iron oxides), Mica, CI 77891 (Titanium dioxide)
Colorona® Bright Gold, Merck®, Mica, CI 77891 (Titanium dioxide), CI 77491 (Iron oxides)
Colorona® Blackstar Gold, Merck®, MICA, CI 77499 (IRON OXIDES)

Other particularly preferred color pigments with the trade name Xirona® are for example:
Xirona® Golden Sky, Merck®, Silica, CI 77891 (Titanium Dioxide), Tin Oxide
Xirona® Caribbean Blue, Merck®, Mica, CI 77891 (Titanium Dioxide), Silica, Tin Oxide
Xirona® Kiwi Rose, Merck®, Silica, CI 77891 (Titanium Dioxide), Tin Oxide
Xirona® Magic Mauve, Merck®, Silica, CI 77891 (Titanium Dioxide), Tin Oxide.

In addition, particularly preferred color pigments with the trade name Unipure® are for example:
Unipure® Red LC 381 EM, Sensient® CI 77491 (Iron Oxides), Silica
Unipure® Black LC 989 EM, Sensient®, CI 77499 (Iron Oxides), Silica
Unipure® Yellow LC 182 EM, Sensient®, CI 77492 (Iron Oxides), Silica In a further embodiment, the agent (b) as contemplated herein may also comprise one or more colorant compounds (b3) from the group comprising organic pigments.

The organic pigments as contemplated herein are correspondingly insoluble, organic dyes or color lacquers, which may be selected, for example, from the group of nitroso, nitro-azo, xanthene, anthraquinone, isoindolinone, isoindolinone, quinacridone, perinone, perylene, diketo-pyrrolopyrrole, indigo, thioindigo, dioxazine and/or triarylmethane compounds.

Examples of particularly suitable organic pigments are carmine, quinacridone, phthalocyanine, sorghum, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In a further particularly preferred embodiment, a process as contemplated herein is exemplified in that the agent (b) comprises at least one colorant compound (b3) from the group of organic pigments which is preferably selected from the group of carmine, quinacridone, phthalocyanine, sorghum, blue pigments having the Color Index numbers CI 42090, CI 69800, CI 69825, CI 73000, CI 74100, CI 74160, yellow pigments having the Color Index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a color paint. As contemplated herein, the term color lacquer means particles comprising a layer of absorbed dyes, the unit of particle and dye being insoluble under the above mentioned conditions. The particles can, for example, be inorganic substrates, which can be aluminum, silica, calcium borosilate, calcium aluminum borosilicate or even aluminum.

For example, alizarin color varnish can be used.

Due to their excellent light and temperature resistance, the use of the pigments in agent (b) of the process as contemplated herein is particularly preferred. It is also preferred if the pigments used have a certain particle size. As contemplated herein, it is therefore advantageous if the at least one pigment has an average particle size $D_{50}$ of about 1.0 to about 50 μm, preferably about 5.0 to about 45 μm, preferably about 10 to about 40 μm, about 14 to about 30 μm. The mean particle size $D_{50}$, for example, can be determined using dynamic light scattering (DLS).

The coloring compounds (b3), the coloring compounds from the group of pigments, represent the third ingredient of the agent (b) essential to the present disclosure. The pigment(s) is (are) used very preferably in certain ranges of amounts in the agent (b). Particularly good results were obtained when the agent (b)—based on the total weight of the agent (b)—contained one or more pigments (b3) in a total amount of about 0.05 to about 10.0 wt. %, preferably about 0.1 to about 7.0 wt. %, more preferably about 0.2 to about 5.0 wt. % and most preferably about 0.3 to about 3.0 wt. %.

In another very particularly preferred embodiment, an agent as contemplated herein is exemplified in that the agent (b) contains—based on the total weight of the agent (b)—one or more pigments (b3) in a total amount of from about 0.05 to about 10.0 wt. %, preferably from about 0.1 to about 7.0 wt. %, more preferably from about 0.2 to about 5.0 wt. % and very particularly preferably from about 0.3 to about 3.0 wt. %.

As colorant compounds (b3), the agents (b) used in the process of the present disclosure may also contain one or more direct dyes. Direct-acting dyes are dyes that draw directly onto the hair and do not require an oxidative process to form the color. Direct dyes are usually nitrophenylene diamines, nitroaminophenols, azo dyes, anthraquinones, triarylmethane dyes or indophenols.

The direct dyes within the meaning of the present disclosure have a solubility in water (760 mmHg) at 25° C. of more than 0.5 g/L and are therefore not to be regarded as pigments.

Preferably, the direct dyes within the meaning of the present disclosure have a solubility in water (760 mmHg) at 25° C. of more than 1.0 g/L.

Direct dyes can be divided into anionic, cationic and non-ionic direct dyes.

In a further embodiment, a process as contemplated herein is exemplified in that the agent (b) comprises at least one colorant compound (b3) from the group of anionic, nonionic and cationic direct dyes.

Suitable cationic direct dyes include Basic Blue 7, Basic Blue 26, HC Blue 16, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51 Basic Red 76.

As non-ionic direct dyes, non-ionic nitro and quinone dyes and neutral azo dyes can be used. Suitable non-ionic direct dyes are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol.

Anionic direct dyes are also called acid dyes. Acid dyes are direct dyes that have at least one carboxylic acid group (—COOH) and/or one sulphonic acid group (—SO$_3$H). Depending on the pH value, the protonated forms (—COOH, —SO$_3$H) of the carboxylic acid or sulphonic acid groups are in equilibrium with their deprotonated forms (—COO$^-$, —SO$_3^-$ present). The proportion of protonated forms increases with decreasing pH. If direct dyes are used in the form of their salts, the carboxylic acid groups or sulphonic acid groups are present in deprotonated form and are neutralized with corresponding stoichiometric equivalents of cations to maintain electro neutrality. Acid dyes can also be used in the form of their sodium salts and/or their potassium salts.

The acid dyes within the meaning of the present disclosure have a solubility in water (760 mmHg) at 25° C. of more than 0.5 g/L and are therefore not to be regarded as pigments. Preferably the acid dyes within the meaning of the present disclosure have a solubility in water (760 mmHg) at 25° C. of more than 1.0 g/L.

The alkaline earth salts (such as calcium salts and magnesium salts) or aluminum salts of acid dyes often have a lower solubility than the corresponding alkali salts. If the solubility of these salts is below 0.5 g/L (25° C., 760 mmHg), they do not fall under the definition of a direct dye.

An essential feature of acid dyes is their ability to form anionic charges, whereby the carboxylic acid or sulphonic acid groups responsible for this are usually linked to different chromophoric systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

In another embodiment, a process for dyeing keratinous material is exemplified in that the agent (b) comprises at least one anionic direct dye (b3) selected from the group of the nitrophenylenediamines, the nitroaminophenols, the azo dyes, the anthraquinone dyes, the triarylmethane dyes, the xanthene dyes the rhodamine dyes, the oxazine dyes and/or the indophenol dyes, the dyes from the abovementioned group each having at least one carboxylic acid group (—COOH), a sodium carboxylate group (—COONa), a potassium carboxylate group (—COOK), a sulfonic acid group (—SO$_3$H), a sodium sulfonate group (—SO$_3$Na) and/or a potassium sulfonate group (—SO$_3$K).

Suitable acid dyes may include, for example, one or more compounds selected from the following group: Acid Yellow 1 (D&C Yellow 7, Citronin A, Ext. D&C Yellow No. 7, Japan Yellow 403,CI 10316, COLIPA n° B001), Acid Yellow 3 (COLIPA n°: C 54, D&C Yellow N° 10, Quinoline Yellow, E104, Food Yellow 13), Acid Yellow 9 (CI 13015), Acid Yellow 17 (CI 18965), Acid Yellow 23 (COLIPA n° C. 29, Covacap Jaune W 1100 (LCW), Sicovit Tartrazine 85 E 102 (BASF®), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA n° C.015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1;CI 20170;KATSU201;nosodiumsalt; Brown No. 201;RESORCIN BROWN;ACID ORANGE 24;Japan Brown 201;D & C Brown No. 1), Acid Red 14 (C.I.14720), Acid Red 18 (E124, Red 18; CI 16255), Acid Red 27 (E 123, CI 16185, C-Rot 46, Real red D, FD&C Red Nr.2, Food Red 9, Naphthol red S), Acid Red 33 (Red 33, Fuchsia Red, D&C Red 33, CI 17200), Acid Red 35 (CI C.I.18065), Acid Red 51 (CI 45430, Pyrosin B, Tetraiodofluorescein, Eosin J, Iodeosin), Acid Red 52 (CI 45100, Food Red 106, Solar Rhodamine B, Acid Rhodamine B, Red n° 106 Pontacyl Brilliant Pink), Acid Red 73 (CI 27290), Acid Red 87 (Eosin, CI 45380), Acid Red 92 (COLIPA n° C53, CI 45410), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet n° 2, C.I. 60730, COLIPA n° C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent Blue AE, Amido blue AE, Erioglaucine A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I.42100), Acid Green 22 (C.I.42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black n° 401, Naphthalene Black 10B, Amido Black 10B, CI 20 470, COLIPA n° B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

For example, the water solubility of anionic direct dyes can be determined in the following way. 0.1 g of the anionic direct dye is placed in a beaker. A stir-fish is added. Then add 100 ml of water. This mixture is heated to 25° C. on a magnetic stirrer while stirring. It is stirred for 60 minutes. The aqueous mixture is then visually assessed. If there are still undissolved radicals, the amount of water is increased—for example in steps of 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml water at 25° C., the solubility of the dye is 1.0 g/L.

Acid Yellow 1 is called 8-hydroxy-5,7-dinitro-2-naphthalenesulfonic acid disodium salt and has a solubility in water of at least 40 g/L (25° C.).

Acid Yellow 3 is a mixture of the sodium salts of mono- and sisulfonic acids of 2-(2-quinolyl)-1H-indene-1,3(2H)-dione and has a water solubility of 20 g/L (25° C.).

Acid Yellow 9 is the disodium salt of 8-hydroxy-5,7-dinitro-2-naphthalenesulfonic acid, its solubility in water is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is highly soluble in water at 25° C.

Acid Orange 7 is the sodium salt of 4-[(2-hydroxy-1-naphthyl)azo]benzene sulphonate. Its water solubility is more than 7 g/L (25° C.).

Acid Red 18 is the trinatirum salt of 7-hydroxy-8-[(E)-(4-sulfonato-1-naphthyl)-diazenyl)]-1,3-naphthalene disulfonate and has a very high water solubility of more than 20 wt. %.

Acid Red 33 is the diantrium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl)benzoic acid, whose solubility in water is indicated as greater than 10 g/L (25° C.).

Acid Blue 9 is the disodium salt of 2-({4-[N-ethyl(3-sulfonatobenzyl]amino]phenyl}{4-[(N-ethyl(3-sulfonatobenzyl)imino]-2,5-cyclohexadien-1-ylidene}methyl)-benzenesulfonate and has a solubility in water of more than 20 wt. % (25° C.).

In a further embodiment, a process as contemplated herein is therefore exemplified in that the agent (b) comprises at least one direct dye (b3) selected from the group of acid yellow 1, acid yellow 3, acid yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The direct dye(s) can be used in different amounts in the agent (b), depending on the desired color intensity. Good results could be obtained if the agent (b)—based on the total weight of the agent (b)—contains one or more direct dyes (b3) in a total amount of from about 0.01 to about 10.0 wt. %, preferably from about 0.1 to about 8.0 wt. %, more preferably from about 0.2 to about 6.0 wt. % and most preferably from about 0.5 to about 4.5 wt. %.

Furthermore, the agent (b) may also contain at least one photochromic or thermochromic dye as the coloring compound (b3).

Photochromic dyes are dyes that react to irradiation with UV light (sunlight or black light) with a reversible change in hue. In this process, the UV light changes the chemical structure of the dyes and thus their absorption behavior (photochromism).

Thermochromic dyes are dyes that react to temperature changes with a reversible change in hue. In this process, the change in temperature alters the chemical structure of the dyes and thus their absorption behavior (Thermochromism).

Agent (b) may contain—based on the total weight of agent (b)—one or more photochromic dyes (b3) in a total amount of from about 0.01 to about 10.0 wt. %, preferably from about 0.1 to about 8.0 wt. %, more preferably from about 0.2 to about 6.0 wt. % and most preferably from about 0.5 to about 4.5 wt. %.

Agent (b) may contain—based on the total weight of agent (b)—one or more thermochromic dyes (b3) in a total amount of from about 0.01 to about 10.0 wt. %, preferably from about 0.1 to about 8.0 wt. %, more preferably from about 0.2 to about 6.0 wt. % and most preferably from about 0.5 to about 4.5 wt. %.

Surfactants in the Agent (b)

Due to its content of water (b1) and fat component (b2), the agent (b) is in the form of an emulsion. To further optimize the formation of the emulsion, it has proven particularly preferable to continue to use at least one surfactant in the agent (b).

Quite preferably, therefore, the agent (b) additionally contains at least one surfactant.

In the context of a further particularly preferred embodiment, a process as contemplated herein is exemplified in that the agent (b) comprises at least one surfactant.

The term surfactants (T) refer to surface-active substances that can form adsorption layers on surfaces and interfaces or aggregate in bulk phases to form micelle colloids or lyotropic mesophases. A distinction is made between anionic surfactants comprising a hydrophobic residue and a negatively charged hydrophilic head group, amphoteric surfactants, which carry both a negative and a compensating positive charge, cationic surfactants, which in addition to a hydrophobic residue have a positively charged hydrophilic group, and non-ionic surfactants, which have no charges but strong dipole moments and are strongly hydrated in aqueous solution.

In a very particularly preferred embodiment, a process as contemplated herein is exemplified in that the agent (b) comprises at least one nonionic surfactant (b4).

Non-ionic surfactants contain, for example, a polyol group, a polyalkylene glycol ether group or a combination of polyol and polyglycol ether group as the hydrophilic group. Such links include Addition products of about 2 to about 50 mol ethylene oxide and/or 0 to about 5 mol propylene oxide to linear and branched fatty alcohols with about 6 to about 30 C atoms, the fatty alcohol polyglycol ethers or the fatty alcohol polypropylene glycol ethers or mixed fatty alcohol polyethers, Addition products of about 2 to about 50 mol ethylene oxide and/or 0 to about 5 mol propylene oxide to linear and branched fatty acids with about 6 to about 30 C atoms, the fatty acid polyglycol ethers or the fatty acid polypropylene glycol ethers or mixed fatty acid polyethers, Addition products of about 2 to about 50 mol ethylene oxide and/or 0 to about 5 mol propylene oxide to linear and branched alkylphenols having about 8 to about 15 C atoms in the alkyl group, the alkylphenol polyglycol ethers or the alkylpolypropylene glycol ethers or mixed alkylphenol polyethers, with a methyl or $C_2$-$C_6$-alkyl radical end-group capped addition products of about 2 to about 50 moles of ethylene oxide and/or 0 to about 5 moles of propylene oxide to linear and branched fatty alcohols with about 8 to about 30 C atoms, to fatty acids with about 8 to about 30 C atoms and to alkylphenols with about 8 to about 15 C atoms in the alkyl group, such as the grades available under the sales names Dehydol® LS, Dehydol® LT (Cognis), $C_{12}$-$C_{30}$ fatty acid mono- and diesters of addition products of about 1 to about 30 mol ethylene oxide to glycerol, Addition products of about 5 to about 60 mol ethylene oxide to castor oil and hardened castor oil, Polyol fatty acid esters, such as the commercial product Hydagen® HSP (Cognis) or Sovermol® grades (Cognis), alkoxylated triglycerides, alkoxylated fatty acid alkyl esters of the formula (Tnio-1)

(Tnio-1)

in which $R^1CO$ is a linear or branched, saturated and/or unsaturated acyl radical having about 6 to about 22 carbon atoms, $R^2$ is hydrogen or methyl, $R^3$ is linear or branched alkyl radicals having 1 to 4 carbon atoms and w is numbers from 1 to about 20, amine oxides, Hydroxy mixed ethers, as described for example in DE-OS 19738866, Sorbitan fatty acid esters and addition products of ethylene oxide to sorbitan fatty acid esters such as polysorbates, Sugar fatty acid esters and addition products of ethylene oxide to sugar fatty acid ester, Addition products of ethylene oxide to fatty acid alkanolamides and fatty amines, Sugar tensides of the alkyl and alkenyl oligoglycoside type according to formula (Tnio-2), $$R^4O\text{---}[G]_p \tag{Tnio-2}$$

in which $R^4$ is an alkyl or alkenyl radical containing 4 to about 22 carbon atoms, G is a sugar residue containing 5 or 6 carbon atoms and p is a number from 1 to about 10. They can be obtained by the relevant methods of preparative organic chemistry. The alkyl and alkenyl oligoglycosides can be derived from aldoses or ketoses with 5 or 6 carbon atoms, preferably glucose. The preferred alkyl and/or alkenyl oligoglycosides are thus alkyl and/or alkenyl oligoglucosides. The index number p in the general formula (Tnio-2) indicates the degree of oligomerization (DP), i.e., the distribution of mono- and oligoglycosides and stands for a number between 1 and 10. While p must always be an integer in the individual molecule and can assume the values p=1 to 6, the value p for a certain alkyl oligoglycoside is an analytically determined arithmetical quantity, which usually represents a fractional number. Preferably alkyl and/or alkenyl oligoglycosides with an average degree of oligomerization p of about 1.1 to about 3.0 are used. From an application technology point of view, those alkyl and/or alkenyl oligoglycosides are preferred whose degree of oligomerization is less than about 1.7 and lies between about 1.2 and about 1.4. The alkyl or alkenyl radical $R^4$ can be derived from primary alcohols containing 4 to about 11, preferably about 8 to about 10 carbon atoms. Typical examples are butanol, caproic alcohol, caprylic alcohol, caprin alcohol and undecrylic alcohol as well as their technical mixtures, such as those obtained in the hydrogenation of technical fatty acid methyl esters or during the hydrogenation of aldehydes from Roelen's oxo synthesis. Preferred are alkyl oligoglucosides with a chain length of $C_8$-$C_{10}$ (DP=1 to 3), which are obtained as a preliminary step in the distillative separation of technical $C_8$-$C_{18}$ coconut-fatty alcohol and may be contaminated with less than about 6 wt. % of $C_{12}$ alcohol, and alkyl oligoglucosides based on technical $C_{9/11}$ oxoalcohols (DP=about 1 to about 3). The alkyl or alkenyl radical $R^{15}$ can also be derived from primary alcohols having about 12 to about 22, preferably about 12 to about 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and their technical mixtures, which can be obtained as described above. Preferred are alkyl oligoglucosides based on hardened $C_{12/14}$ coconut alcohol with a DP of about 1 to about 3.

Sugar surfactants of the fatty acid N-alkyl polyhydroxyalkylamide type, a nonionic surfactant of formula (Tnio-3)

$$R^5CO\text{---}NR^6\text{---}[Z] \tag{Tnio-3}$$

in which $R^5CO$ is an aliphatic acyl radical containing about 6 to about 22 carbon atoms, $R^6$ is hydrogen, an alkyl or hydroxyalkyl radical containing 1 to 4 carbon atoms and [Z] is a linear or branched polyhydroxyalkyl radical containing 3 to about 12 carbon atoms and 3 to about 10 hydroxyl groups. The fatty acid N-alkyl polyhydroxyalkylamides are known substances that can usually be obtained by reductive amination of a reducing sugar with ammonia, an alkylamine or an alkanolamine and subsequent acylation with a fatty acid, a fatty acid alkyl ester or a fatty acid chloride. The fatty acid N-alkyl polyhydroxyalkylamides are preferably derived from reducing sugars with 5 or 6 carbon atoms, especially from glucose. The preferred fatty acid N-alkyl polyhydroxyalkylamides are therefore fatty acid N-alkylglucamides as represented by the formula (Tnio-4):

$$R^7CO\text{---}(NR^8)\text{---}CH_2\text{---}[CH(OH)]_4\text{---}CH_2OH \tag{Tnio-4}$$

Preferably, glucamides of the formula (Tnio-4) are used as fatty acid-N-alkyl polyhydroxyalkylamides, in which $R^8$ represents hydrogen or an alkyl group and $R^7CO$ represents the acyl radical of caproic acid, caprylic acid, capric acid, Lauric acid, myristic acid, palmitic acid, palmoleic acid, stearic acid, isostearic acid, oleic acid, elaidic acid, petroselinic acid, linoleic acid, linolenic acid, arachidic acid, gadoleic acid, behenic acid or erucic acid or their technical mixtures. Particularly preferred are fatty acid N-alkyl glucamides of the formula (Tnio-4), which are obtained by reductive amination of glucose with methylamine and subsequent acylation with lauric acid or C12/14 coconut fatty acid or a corresponding derivative. Furthermore, polyhydroxyalkylamides can also be derived from maltose and palatinose.

The sugar surfactants may preferably be present in the agent used as contemplated herein in amounts of about 0.1-about 20 wt. %, based on the total agent. Amounts of about 0.5-about 15 wt. % are preferred and amounts of about 0.5-about 7.5 wt. % are particularly preferred.

Other typical examples of nonionic surfactants are fatty acid amide polyglycol ethers, fatty amine polyglycol ethers, mixed ethers or mixed formals, protein hydrolysates (especially wheat-based vegetable products) and polysorbates.

The alkylene oxide addition products to saturated linear fatty alcohols and fatty acids, each with about 2 to about 30 moles of ethylene oxide per mole of fatty alcohol or fatty acid, and the sugar surfactants have proved to be preferred nonionic surfactants. Preparations with excellent properties are also obtained if they contain fatty acid esters of ethoxylated glycerol as non-ionic surfactants.

These connections are identified by the following parameters. The alkyl radical R contains about 6 to about 22 carbon atoms and can be either linear or branched. Primary linear and in 2-position methyl-branched aliphatic radicals are preferred. Such alkyl radicals are for example 1-octyl, 1-decyl, 1-lauryl, 1-myristyl, 1-cytyl and 1-stearyl. Especially preferred are 1-octyl, 1-decyl, 1-lauryl, 1-myristyl. When so-called "oxo-alcohols" are used as starting materials, compounds with an odd number of carbon atoms in the alkyl chain predominate.

The compounds with alkyl groups used as surfactants can each be uniform substances. However, it is usually preferable to start from native plant or animal raw materials in the production of these substances, so that one obtains substance mixtures with different alkyl chain lengths depending on the respective raw material.

For surfactants which are products of the addition of ethylene and/or propylene oxide to fatty alcohols or derivatives of these addition products, both products with a "normal" homologue distribution and those with a narrowed homologue distribution can be used. By "normal" homologue distribution we mean mixtures of homologues obtained in the reaction of fatty alcohol and alkylene oxide using alkali metals, alkali metal hydroxides or alkali metal alcoholates as catalysts. Constricted homologue distributions are obtained, on the other hand, when, for example, hydrotalcites, alkaline earth metal salts of ether carboxylic acids, alkaline earth metal oxides, hydroxides or alcoholates are used as catalysts. The use of products with narrowed homologue distribution may be preferred.

Particularly good results were obtained when an agent (b) containing at least one ethoxylated fatty alcohol with a degree of ethoxylation of about 10 to about 40 was used in the process as contemplated herein.

In another very particularly preferred embodiment, a process as contemplated herein is exemplified in that the agent (b) comprises at least one nonionic surfactant (b4) of the formula (T-I),

wherein
Rb is a saturated or unsaturated, unbranched or branched $C_8$-$C_{24}$ alkyl group, preferably a saturated, unbranched $C_{16}$- to $C_{18}$ alkyl group, and
m an integer from about 10 to about 40, preferably an integer from about 20 to about 35, and particularly preferably the number 30.

A particularly well-suited nonionic surfactant of this type is ceteareth-30. Ceteareth-30 is a mixture of cetyl alcohol and stearyl alcohol, each ethoxylated with 30 units of ethylene oxide. The mixture of cetyl alcohol and stearyl alcohol is called cetearyl alcohol. Ceteareth-30 has the CAS number 68439-49-6 and can be purchased, for example, under the trade name Eumulgin® B3 from BASF®.

The nonionic surfactants, in particular the nonionic surfactants of formula (T-I), are preferably used in the appropriate amount ranges in agent (b). Thus, based on the total weight of agent (b), agent (b) may contain one or more nonionic surfactants in a total amount of from about 0.1 to about 20 wt. %, preferably from about 0.2 to about 10 wt. %, more preferably from about 0.3 to about 5 wt. %, and most preferably from about 0.4 to about 2.5 wt. %.

Amino Silicones not Used in the Agent (b)

In step (3) of the process as contemplated herein, the agents (a) and (b) are mixed and in this way a ready-to-use colorant is prepared, which is then applied to the hair (step (4)), allowed to act (step (5)) and rinsed out again (step (6)).

As described above, the agent (a) is preferably the concentrate of an amino silicone (a1), which meets the colorant compounds (i.e., the pigments) (b3) only shortly before application. Mixing initiates the reaction or interaction of the amino silicones (a1) with the pigments (b3), which under the conditions of use ultimately leads to conglomeration, accumulation or aggregation of (a1) and (b3) and in this way presumably immobilizes the pigments on the surface of the keratin fibers.

To enable a homogeneous color result on the keratin fiber, it has been found essential in this context that this interaction of (a1) and (b3) is started only shortly before or during the dyeing process and that a common storage of (a1) and (b3) is avoided. For this reason, it has further been found to be quite particularly preferred if the agent (b) itself does not contain any amino silicones.

In a further explicitly quite particularly preferred embodiment, a process as contemplated herein is exemplified in that the total content of amino-functionalized silicone polymers in the agent (b)—based on the total weight of the agent (b)—is below about 1.0 wt. %, preferably below about 0.5 wt. %, more preferably below about 0.1 wt. % and very particularly preferably below about 0.01 wt. %.

In other words, in a further explicitly quite particularly preferred embodiment, a process as contemplated herein is exemplified in that the agent (b) contains—based on the total weight of the agent (a)—one or more amino-functionalized silicone polymers in a total amount of from 0 to about 1.0 wt. %, preferably from 0 to about 0.5 wt. %, more preferably from 0 to about 0.1 wt. % and very particularly preferably from 0 to about 0.01 wt. %.

It is explicitly quite preferred if the agent (b) does not contain any amino-functionalized silicone polymers.

Further Optional Ingredients in the Agents (a) and/or (b)

In addition to the ingredients essential to the present disclosure already described, agents (a) and/or (b) may also contain other optional ingredients.

For example, agents (a) and/or (b) may contain a film-forming polymer. The film-forming polymer may be selected, for example, from the group comprising polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinyl caprolactam copolymers, vinylpyrrolidone/vinylformamide copolymers and/or vinylpyrrolidone/vinyl alcohol copolymers, explicitly very particularly preferred polyvinylpyrrolidone (PVP).

Further suitable film-forming polymers can be selected from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

Film-forming polymers selected from the group of synthetic polymers, polymers obtainable by free-radical polymerization, or natural polymers have proven to be well suited.

Other particularly well-suited film-forming polymers can be selected from the homopolymers or copolymers of olefins, such as cycloolefins, butadiene, isoprene or styrene, vinyl ethers, vinyl amides, the esters or amides of (meth) acrylic acid having at least one $C_1$-$C_{20}$ alkyl group, an aryl group or a C2-C10 hydroxyalkyl group.

Other film-forming polymers may be selected from the homo- or copolymers of isooctyl (meth)acrylate; isononyl (meth)acrylate; 2-ethylhexyl (meth)acrylate; lauryl (meth) acrylate); isopentyl (meth)acrylate; n-butyl (meth)acrylate); isobutyl (meth)acrylate; ethyl (meth)acrylate; methyl (meth) acrylate; tert-butyl (meth)acrylate; stearyl (meth)acrylate; hydroxyethyl (meth)acrylate; 2-hydroxypropyl (meth)acrylate; 3-hydroxypropyl (meth)acrylate; and/or mixtures thereof.

Further film-forming polymers may be selected from the homo- or copolymers of (meth)acrylamide; N-alkyl-(meth) acrylamides, in particular those with C2-C18 alkyl groups, such as N-ethyl-acrylamide, N-tert-butyl-acrylamide, N-octyl-acrylamide; N-di(C1-C4)alkyl-(meth)acrylamide.

Other preferred anionic copolymers are, for example, copolymers of acrylic acid, methacrylic acid or their $C_1$-$C_6$ alkyl esters, as they are marketed under the INCI Declaration Acrylates Copolymers. A suitable commercial product is for example Aculyn® 33 from Rohm & Haas. Copolymers of acrylic acid, methacrylic acid or their $C_1$-$C_6$ alkyl esters and the esters of an ethylenically unsaturated acid and an alkoxylated fatty alcohol are also preferred. Suitable ethylenically unsaturated acids are especially acrylic acid, methacrylic acid and itaconic acid; suitable alkoxylated fatty alcohols are especially steareth-20 or ceteth-20.

Very particularly preferred polymers on the market are, for example, Aculyn® 22 (Acrylates/Steareth-20 Methacrylate Copolymer), Aculyn® 28 (Acrylates/Beheneth-25 Methacrylate Copolymer), Structure 2001® (Acrylates/Steareth-20 Itaconate Copolymer), Structure 3001® (Acrylates/Ceteth-20 Itaconate Copolymer), Structure Plus® (Acrylates/Aminoacrylates C10-30 Alkyl PEG-20 Itaconate Copolymer), Carbopol® 1342, 1382, Ultrez 20, Ultrez 21 (Acrylates/C10-30 Alkyl Acrylate Crosspolymer), Synthalen W 2000® (Acrylates/Palmeth-25 Acrylate Copolymer) or the Rohme and Haas distributed Soltex OPT (Acrylates/C12-22 Alkyl methacrylate Copolymer).

The homo- and copolymers of N-vinylpyrrolidone, vinylcaprolactam, vinyl-(C1-C6)alkyl-pyrrole, vinyl-oxazole, vinyl-thiazole, vinylpyrimidine, vinylimidazole can be named as suitable polymers based on vinyl monomers.

Furthermore, the copolymers octylacrylamide/acrylates/butylaminoethyl-methacrylate copolymer, as commercially marketed under the trade names AMPHOMER® or LOVOCRYL® 47 by NATIONAL STARCH, or the copolymers of acrylates/octylacrylamides marketed under the trade names DERMACRYL® LT and DERMACRYL® 79 by NATIONAL STARCH are particularly suitable.

Suitable olefin-based polymers include homopolymers and copolymers of ethylene, propylene, butene, isoprene and butadiene.

In another version, block copolymers can be used as film-forming hydrophobic polymers, which comprise at least one block of styrene or the derivatives of styrene. These block copolymers can be copolymers that contain one or more other blocks in addition to a styrene block, such as styrene/ethylene, styrene/ethylene/butylene, styrene/butylene, styrene/isoprene, styrene/butadiene. Such polymers are commercially distributed by BASF® under the trade name "Luvitol HSB".

In a further embodiment, a process as contemplated herein is exemplified in that the agent (a) and/or (b) comprises at least one film-forming polymer selected from the group of polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers, the copolymers of acrylic acid, of copolymers of methacrylic acid, of homopolymers or copolymers of acrylic acid esters, of homopolymers or copolymers of methacrylic acid esters, of homopolymers or copolymers of acrylic acid amides, of homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

The film-forming polymer or polymers are preferably used in specific ranges of amounts in agents (a) and/or (b). In this context, it has proved to be particularly preferred for the solution of the task as contemplated herein if the agent (b)—based on the total weight of agent (b)—contains one or more polymers in a total amount of about 0.1 to about 25.0 wt. %, preferably from about 0.2 to about 20.0 wt. %, more preferably from about 0.5 to about 15.0 wt. % and very particularly preferably from about 1.0 to about 7.0 wt. %.

The agents may also contain one or more surfactants. The term surfactants refer to surface-active substances. A distinction is made between anionic surfactants comprising a hydrophobic residue and a negatively charged hydrophilic head group, amphoteric surfactants, which carry both a negative and a compensating positive charge, cationic surfactants, which in addition to a hydrophobic residue have a positively charged hydrophilic group, and non-ionic surfactants, which have no charges but strong dipole moments and are strongly hydrated in aqueous solution.

Zwitterionic surfactants are those surface-active compounds which carry at least one quaternary ammonium group and at least one —$COO^{(-)}$- or —$SO_3^{(-)}$ group in the molecule. Particularly suitable zwitterionic surfactants are the so-called betaines such as the N-alkyl-N,N-dimethylammonium-glycinate, for example the cocoalkyl-dimethylammoniumglycinate, N-acylaminopropyl-N,N-dimethylammoniumglycinate, for example, cocoacylaminopropyl dimethyl ammonium glycinate, and 2-alkyl-3-carboxymethyl-3-hydroxyethyl imidazolines each having about 8 to about 18 C atoms in the alkyl or acyl group, and cocoacylaminoethyl hydroxyethyl carboxymethyl glycinate. A preferred zwitterionic surfactant is the fatty acid amide derivative known under the INCI name cocamidopropyl betaine.

Ampholytic surfactants are surface-active compounds which, apart from a $C_8$-$C_{24}$ alkyl or acyl group, contain at least one free amino group and at least one —COOH— or —$SO_3H$ group in the molecule and can form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each with about 8 to 24 C atoms in the alkyl group. Typical examples of amphoteric or zwitterionic surfactants are alkylbetaines, alkylamidobetaines, amino-propionates, aminoglycinate, imidazoliniumbetaines and sulfobetaines.

Particularly preferred ampholytic surfactants are N-cocoalkylaminopropionate, cocoacylaminoethylaminopropionate and $C_{12}$-$C_{18}$ acylsarcosine.

In addition, the agents may also contain at least one cationic surfactant. Cationic surfactants are surfactants, i.e., surface-active compounds, each with one or more positive charges. Cationic surfactants contain only positive charges. Usually, these surfactants are composed of a hydrophobic part and a hydrophilic head group, the hydrophobic part usually comprising a hydrocarbon backbone (e.g., comprising one or two linear or branched alkyl chains) and the positive charge(s) being in the hydrophilic head group. Examples of cationic surfactants are quaternary ammonium compounds which, as hydrophobic radicals, may carry one or two alkyl chains with a chain length of about 8 to about 28 C atoms, quaternary phosphonium salts substituted with one or more alkyl chains with a chain length of about 8 to about 28 C atoms or tertiary sulfonium salts.

Furthermore, the cationic charge can also be part of a heterocyclic ring (e.g., an imidazolium ring or a pyridinium ring) in the form of an onium structure. In addition to the functional unit carrying the cationic charge, the cationic surfactant may also contain other uncharged functional groups, as is the case for example with esterquats. The cationic surfactants are used in a total quantity of about 0.1 to about 45 wt. %, preferably about 1 to about 30 wt. % and most preferably about 1 to about 15 wt. %—based on the total weight of the respective agent.

Furthermore, the agent as contemplated herein may also contain at least one anionic surfactant. Anionic surfactants are surface-active agents with exclusively anionic charges (neutralized by a corresponding counter cation). Examples of anionic surfactants are fatty acids, alkyl sulphates, alkyl ether sulphates and ether carboxylic acids with about 12 to about 20 C atoms in the alkyl group and up to about 16 glycol ether groups in the molecule.

The anionic surfactants are used in a total quantity of about 0.1 to about 45 wt. %, preferably about 1 to about 30 wt. % and most preferably about 1 to about 15 wt. %—based on the total weight of the respective agent.

The agents may also contain other active ingredients, auxiliaries and additives, such as solvents; fatty ingredients such as $C_8$-$C_{30}$ fatty alcohols, $C_8$-$C_{30}$ fatty acid triglycerides, $C_8$-$C_{30}$ fatty acid monoglycerides, $C_8$-$C_{30}$ fatty acid diglycerides and/or hydrocarbons; polymers; structurants such as glucose, maleic acid and lactic acid, hair conditioning compounds such as phospholipids, for example lecithin and cephalins; perfume oils, dimethyl isosorbide and cyclodextrins; fiber structure-improving active ingredients, in particular mono-, di- and oligosaccharides such as glucose, galactose, fructose, fructose and lactose; dyes for coloring the product; anti-dandruff active ingredients such as piroctone olamine, zinc omadine and climbazole; amino acids and oligopeptides; protein hydrolysates on an animal and/or vegetable basis, as well as in the form of their fatty acid condensation products or optionally anionically or cationically modified derivatives; vegetable oils; light stabilizers and UV blockers; active ingredients such as panthenol, pantothenic acid, pantolactone, allantoin, pyrrolidinonecarboxylic acids and their salts, and bisabolol; Polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; ceramides or pseudoceramides; vitamins, provitamins and vitamin precursors; plant extracts; Fats and waxes such as fatty alcohols, beeswax, montan wax and kerosene; swelling and penetrating agents such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescing agents such as ethylene glycol mono- and distearate and PEG-3 distearate; and blowing agents such as propane-butane mixtures, N20, dimethyl ether, CO2 and air.

The selection of these other substances will be made by the specialist according to the desired properties of the agents. Regarding other optional components and the quantities of these components used, explicit reference is made to the relevant manuals known to the specialist. The additional active ingredients and auxiliary substances are preferably used in the preparations as contemplated herein in quantities of about 0.0001 to about 25 wt. % each, about 0.0005 to about 15 wt. %, based on the total weight of the respective agent.

As described above, however, the agent (a) particularly preferably comprises essentially the ingredients (a1) plus, if appropriate, solvent. If the agent (a) should also contain any of the other optional ingredients described above, these are particularly preferably used in the agent (a) only in very small amounts.

Preparation of the Application Mixture by Mixing the Agents (a) and (b).

In step (3) of the process as contemplated herein, a ready-to-use mixture is prepared by mixing agents (a) and (b). In other words, in this process step the concentrate (a), i.e., the preferably low-water, highly concentrated admixture of amino silicone (a1), is mixed with an emulsion, the emulsion comprising the components (b1), (b2) and (b3).

In principle, different quantities of agent (a) can be mixed with agent (b), so that mixing ratios (a)/(b) of about 1:400 to about 400:1 are conceivable.

However, since the agent (a) is preferably a concentrate, it has proved particularly preferable to use the agent (a) in small amounts and to dilute these with comparatively higher amounts of the colorant (b).

It is particularly preferred if the application mixture is prepared by mixing agents (a) and (b) in a quantity ratio (a)/(b) of from about 1:5 to about 1:200, preferably from about 1:10 to about 1:150, further preferably from about 1:20 to about 1:140 and most preferably from about 1:40 to about 1:110.

For example, with a quantity ratio (a)/(b) of 1:120, 1 g of agent (a) can be mixed with 120 g of agent (b).
For example, with a quantity ratio (a)/(b) of 1:100, 1 g of agent (a) can be mixed with 100 g of agent (b).
For example, with a quantity ratio (a)/(b) of 1:15, 15 g of agent (a) can be mixed with 75 g of agent (b).
For example, with a quantity ratio (a)/(b) of 1:25, 4 g of agent (a) can be mixed with 100 g of agent (b).

Within the scope of a further preferred embodiment, a method as contemplated herein is exemplified by the
(3) Preparation of an application mixture by mixing the agents (a) and (b) in a quantity ratio (a)/(b) of from about 1:5 to about 1:200, preferably from about 1:10 to about 1:150, more preferably from about 1:20 to about 1:140 and most preferably from about 1:40 to about 1:110.

The pH values of agents (a) and (b) are preferably adjusted so that the application mixture prepared from (a) and (b) also has a neutral to alkaline pH value. Most preferably, the application mixture has an alkaline pH in the range of about 7.0 to about 11.5 preferably from about 8.0 to about 11.0, and most preferably from about 8.5 to about 10.5. Under basic conditions, the amino-functionalized silicone polymer (a1) can be dissolved or dispersed particularly well and without protonation.

Within the scope of a further preferred embodiment, a process as contemplated herein is exemplified in that the application mixture prepared by mixing agents (a) and (b) has a pH of from about 7.0 to about 11.5, preferably from about 8.0 to about 11.0, and particularly preferably from about 8.5 to about 10.5.

To adjust the desired pH, the agent (a) and/or (b) may contain at least one alkalizing agent. The pH values for the purposes of the present disclosure are pH values measured at a temperature of 22° C.

As alkalizing agents, the agents may contain, for example, ammonia, alkanolamines and/or basic amino acids.

The alkanolamines which can be used in the agent of the present disclosure are preferably selected from primary amines having a $C_2$-$C_6$ alkyl base which carries at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

Alkanolamines particularly preferred as contemplated herein are selected from 2-aminoethan-1-ol and/or 2-amino-2-methylpropan-1-ol. A particularly preferred embodiment is therefore exemplified in that the agent as contemplated herein contains an alkanolamine selected from 2-aminoethan-1-ol and/or 2-amino-2-methylpropan-1-ol as alkalizing agent.

For the purposes of the present disclosure, an amino acid is an organic compound containing at least one protonatable amino group and at least one —COOH or —SO$_3$H group in its structure. Preferred amino acids are amino carboxylic acids, especially α-(alpha)-amino carboxylic acids and ω-amino carboxylic acids, whereby α-amino carboxylic acids are particularly preferred.

As contemplated herein, basic amino acids are those amino acids which have an isoelectric point pI of greater than about 7.0.

Basic α-amino carboxylic acids contain at least one asymmetric carbon atom. In the context of the present disclosure, both possible enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine and histidine, especially preferably arginine and lysine. In another particularly preferred embodiment, an agent as contemplated herein is therefore exemplified in that the alkalizing agent is a basic amino acid from the group arginine, lysine, ornithine and/or histidine.

In addition, the product may contain other alkalizing agents, especially inorganic alkalizing agents. Inorganic alkalizing agents usable as contemplated herein are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Particularly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-Amino-2-methylpropan-2-ol, 3-aminopropan-1,2-diol, 2-amino-2-methylpropan-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

In another very particularly preferred embodiment, a process as contemplated herein is exemplified in that the colorant (a) comprises at least one alkalizing agent selected from the group of ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Application of the Application Mixture

In step (4) of the process as contemplated herein, the application mixture prepared in step (3) is applied to the keratinous material, which is very preferably human hair.

Preferably, the application mixture is applied to the keratin material (or to the hair) within a period of about 1 to about 120 minutes, preferably about 1 to about 60 minutes, further preferably about 1 to about 30 minutes, and most preferably about 1 to about 15 minutes after its preparation in step (3).

In a further preferred embodiment, a method as contemplated herein is exemplified by:

(4) Applying application mixture to the keratinous material within a period of from about 1 to about 120 minutes, preferably from about 1 to about 60 minutes, more preferably from about 1 to about 30 minutes, and most preferably from about 1 to about 15 minutes after its preparation in step (3).

Exposure of the Application Mixture to the Keratin Material

In step (5) of the process as contemplated herein, the application mixture is allowed to act on the keratinous material after its application. In this context, different exposure times of, for example, about 30 seconds to about 60 minutes are conceivable.

However, a major advantage of the dyeing system as contemplated herein is that an intensive color result can be achieved even in very short periods after short exposure times. For this reason, it is advantageous if the application mixture remains on the keratin material only for comparatively short periods of time after its application, from about 30 seconds to about 15 minutes, preferably from about 30 seconds to about 10 minutes, and particularly preferably from about 1 to about 5 minutes.

In a further preferred embodiment, a method as contemplated herein is exemplified by:

(5) exposure of the application mixture applied in step (4) to the keratinous material for a period ranging from about 30 seconds to about 15 minutes, preferably from about 30 seconds to about 10 minutes, and more preferably from about 1 to about 5 minutes.

Rinse Out the Application Mixture

Finally, after the application mixture has acted on the keratin material, it is rinsed out with water in step (6).

Here, in one embodiment, the application mixture can be washed out with water only, i.e., without the aid of an after-treatment agent or a shampoo. The use of a post-treatment agent or conditioner in step (6) is also conceivable in principle.

However, to solve the task as contemplated herein and to increase the ease of use, it has proved particularly preferable to rinse the application mixture in step (6) exclusively with water without the aid of a further after-treatment agent, without shampoo and without conditioner.

In a further preferred embodiment, a method as contemplated herein is exemplified by:

(6) Rinse the application mixture with water only.

Sequence of the Process Steps

The method as contemplated herein comprises steps (1) to (6).

In step (1) the agent (a) is provided, step (2) comprises providing the agent (b). These two steps do not necessarily have to take place one after the other but can also run simultaneously.

Thus, step (1) can occur before step (2), steps (1) and (2) can occur simultaneously, or step (2) can occur before step (1).

If, for example, agents (a) and (b) are provided to the user in a multi-component packaging unit, both agents are provided at the same time and it is left to the user to decide which agent to remove first from the packaging.

The preparation of an application mixture by mixing agents (a) and (b) in step (3) can only be carried out after both agents (a) and (b) have been provided The application of the application mixture in step (4) can only take place after its preparation in step (3).

Similarly, the application mixture in step (5) may be applied after it has been applied to the keratin material, and the rinsing of the application mixture in step (6) may be carried out after it has been applied in step (5).

Multi-Component Packaging Unit

To increase user convenience, the user is preferably provided with all the necessary agents in the form of a multi-component packaging unit (kit-of-parts).

A second subject of the present disclosure is therefore a multi-component packaging unit (kit-of-parts) for coloring keratinous material, comprehensively packaged separately from one another a first container containing an agent (a), wherein the agent comprises (a):

(a1) at least one amino-functionalized silicone polymer, and a second container containing an agent (b), wherein the agent comprises (b):

(b1) Water and (b2) at least one fat component and (b3) at least one color-imparting compound, and (b4) optionally at least one non-ionic surfactant, wherein the ingredients (a1), (b1), (b2), (b3) and (b4) are disclosed in detail in the description of the first subject matter of the present disclosure.

The amino-functionalized silicone polymers (a1) contained in agent (a) of the kit correspond to the amino-functionalized silicone polymers (a1) that were also used in agent (a) of the previously described process.

The fat components (b2) contained in the agent (b) of the kit, correspond to the fat components (b2) that were also used in the agent (a) of the previously described process.

The colorant compounds (b3) contained in agent (b) of the kit correspond to the colorant compounds (b3) that were also used in agent (b) of the previously described method.

The nonionic surfactants (b4) optionally contained in the agent (b) of the kit, correspond to the nonionic surfactants (b4) that were also used in the agent (4) of the previously described process.

With respect to the other preferred embodiments of the multi-component packaging unit as contemplated herein, the same applies mutatis mutandis to the procedure as contemplated herein.

Examples

1. Formulations

The following formulations were produced:

| Agent (a) (concentrate) | (aV1) Comparison | (aE1) Present Disclosure |
|---|---|---|
| Unipure ® Red LC3079, organic pigment CI 15850 | 1.0 g | — |
| Dow ® Corning 2-8566 (Siloxanes and Silicones, 3-[(2-Aminoethyl)amino]-2-methylpropyl Me, Di-Me-Siloxane" | 1.0 g | 1.0 g |
| Total amount of concentrate (a) | 2.0 g | 1.0 g |

| Agent (b) Carrier formulation | (bV1) Comparison | (bE1) Present Disclosure |
|---|---|---|
| Cetyl alcohol | 3.0 g | 3.0 g |
| Stearyl alcohol | 3.0 g | 3.0 g |
| Ceteareth-30 (Cetearyl alcohol, ethoxylated 30 EO) | 1.5 g | 1.5 g |
| Potassium hydroxide, 50% aqueous solution | 0.5 g | 0.5 g |
| Unipure ® Red LC3079, organic pigment CI 15850 | — | 1.0 g |
| 1.2-propanediol | 10.0 g | 10.0 g |
| Water | 80 g | 80 g |
| Total quantity carrier-base (b) | 98 g | 99 g |

| Comparison | (V) |
|---|---|
| Cetyl alcohol | 3.0 g |
| Stearyl alcohol | 3.0 g |
| Ceteareth-30, (Cetearyl alcohol, ethoxylated 30 EO) | 1.5 g |
| Potassium hydroxide, 50% aqueous solution | 0.5 g |
| Unipure ® Red LC3079, organic pigment CI 15850 | 1.0 g |
| 1.2-propanediol | 10.0 g |
| Dow ® Corning 2-8566 (Siloxanes and Silicones, 3-[(2-Aminoethyl)amino]-2-methylpropyl Me, Di-Me-Siloxane" | 1.0 g |
| Water | 80 g |
| Total quantity Comparison formulation | 100 g |

All formulations were placed in a glass container, sealed and stored at 25° C. for 8 weeks.

2. Application

The following application mixtures (AWM) were prepared from the stored formulations:

| AWM 1, comparison | AWM 2, comparison | AWM 3, Present Disclosure |
|---|---|---|
| 2 g (aV1) 98 g (bV1) | 100 g (V) | 1 g (aE1) 99 g (bE1) |

Application mixture AWM 1 was prepared by shaking 2 g of the agent (aV1) with 98 g of the agent (bV1) (comparison).

The application mixture AWM 2 is the comparative formulation (V), which was used without further mixing as such after storage (comparison).

Application mixture AWM 3 was prepared by shaking 1 g of agent (aE1) with 99 g of agent (bE1) (present disclosure).

Each application mixture was tested on hair strands (Kerling, Euronatural hair white, liquor ratio: 1 g application mixture per g strand of hair). The application mixture was left to act for three minutes. Subsequently, the hair strand was thoroughly washed (1 minute) with water, dried, and then visually evaluated under the daylight lamp:

|  | AWM 1, Comparison | AWM 2, Comparison | AWM 3, Present Disclosure |
|---|---|---|---|
| Intensity of coloring | high | very low | high |
| Homogeneity of the coloring | low | low | high |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for dyeing keratinous material, the method comprising the steps of:
   (1) providing an agent (a), wherein the agent (a) comprises:
      (a1) at least one amino-functionalized silicone polymer,
      wherein the agent (a) comprises —based on a total weight of the agent (a) —less than about 10.0 wt. % of water,
   (2) providing an agent (b), wherein the agent (b) comprises:
      (b1) water,
      (b2) at least one fat component, and
      (b3) at least one colorant compound,
   (3) preparing an application mixture by mixing agent (a) and agent (b),
   (4) applying the application mixture prepared in step (3) to the keratinous material,
   (5) exposing the application mixture applied in step (4) to the keratinous material; and
   (6) rinsing the application mixture from the keratinous material with water.

2. The method according to claim 1, wherein the at least one amino-functionalized silicone polymer (a1) comprises a secondary amino group.

3. The method according to claim 1, wherein the at least one amino-functionalized silicone polymer (a1) comprises a structural unit of the formula (Si amino),

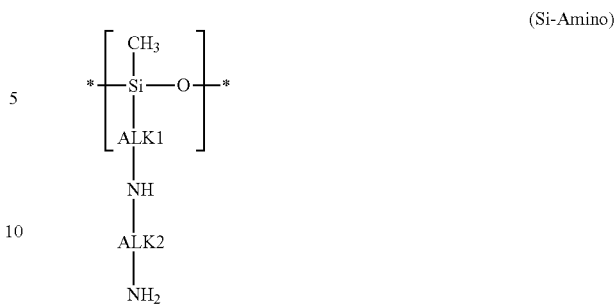

where
   ALK1 and ALK2 independently represent a linear or branched $C_1$-$C_{20}$ divalent alkylene group.

4. The method according to claim 1, wherein the at least one amino-functionalized silicone polymer (a1) comprises structural units of formula (Si-I) and of formula (Si-II)

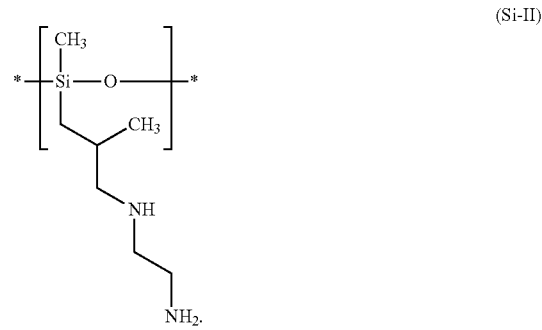

5. The method according to claim 1, wherein the agent (a) comprises —based on a total weight of the agent (a) —the one or more amino-functionalized silicone polymers (a1) in a total amount of from about 5 to about 100 wt. %.

6. The method according to claim 1, wherein the agent (a) comprises based on a total weight of the agent (a) from 0 to about 2.5 wt. % water.

7. The method according to claim 1, wherein the agent (b) comprises —based on a total weight of the agent (b) —about 50.0 to about 98.0 wt. % of the water (b1).

8. The method according to claim 1, wherein the one or more fat components (b2) are selected from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides, hydrocarbons, and combinations thereof.

9. The method according to claim 8, wherein the one or more fat components (b2) comprises the $C_{12}$-$C_{30}$ fatty alcohols, wherein the $C_{12}$-$C_{30}$ fatty alcohols are selected from the group of dodecan-1-ol, tetradecan-1-ol, hexadecan-1-ol, octadecan-1-ol, eicosan-1-ol, heneicosan-1-ol, docosan-1-ol, (9Z)-octadec-9-en-1-ol, (9E)-Octadec-9-en-1-ol, (9Z,12Z)-Octadeca-9,12-dien-1-ol, (9Z,12Z,15Z)-Octadeca-9,12,15-trien-1-ol, (9Z)-Eicos-9-en-1-ol, (5Z,8Z,11Z,14Z)-Eicosa-5, 8,11,14-tetraen-1-ol, (13Z)-docos-13-en-1-ol), (13E)-docosen-1-ol), 2-octyl-dodecanol, 2-hexyl-dodecanol and/or 2-butyl-dodecanol.

10. The method according to claim 1, wherein the at least one colorant compound (b3) is selected from the group of pigments, direct dyes, photochromic dyes, thermochromic dyes, and combinations thereof.

11. The method according to claim 1, wherein the at least one colorant compound (b3) comprises an inorganic pigment, wherein the inorganic pigment is selected from the group of colored metal oxides, metal hydroxides, metal oxide hydrates, silicates, metal sulfides, complex metal cyanides, metal sulfates, bronze pigments, colored mica- or mica-based pigments coated with at least one metal oxide and/or a metal oxychloride, and combinations thereof.

12. The method according to claim 1, wherein the at least one colorant compound (b3) comprises an organic pigment, wherein the organic pigment is selected from the group of carmine, quinacridone, phthalocyanine, sorghum, blue pigments having the Color Index numbers Cl 42090, CI 69800, CI 69825, CI 73000, CI 74100, CI 74160, yellow pigments having the Color Index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470, and combinations thereof.

13. The method according to claim 1, wherein the agent (b) compirses —based on a total weight of the agent (b) —the at least one colorant compound (b3) in a total amount of from about 0.05 to about 10.0 wt. %.

14. The method according to claim 1, wherein the agent (b) comprises at least one nonionic surfactant (b4).

15. The method according to claim 1, wherein the agent (b) comprises at least one nonionic surfactant (b4) of formula (T-I),

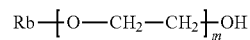 (T-I)

wherein
Rb represents a saturated or unsaturated, unbranched or branched $C_8$-$C_{24}$ alkyl group, and
m represents an integer from about 10 to about 40.

16. The method according to claim 1, wherein
(3) preparing of an application mixture by mixing the agent (a) and agent (b) comprises mixing agent (a) and agent (b) in a quantity ratio (a)/(b) of from about 1:5 to about 1:200.

17. The method according to claim 1, wherein the application mixture prepared by mixing agents (a) and (b) has a pH of from about 7.0 to about 11.5.

18. The method according to claim 1, wherein:
(4) the application mixture is applied to the keratinous material within a period of from about 1 to about 120 minutes after preparation of the application mixture in step (3).

19. The method according to claim 1, wherein:
(5) the application mixture applied in step (4) is exposed to the keratinous material for a period of from about 30 seconds to about 15 minutes.

20. A kit-of-parts for dyeing keratinous material, comprising separately packaged
a first container containing an agent (a), wherein the agent (a) comprises:
(a1) at least one amino-functionalized silicone polymer, wherein the agent (a) comprises —based on a total weight of the agent (a) —less than about 10.0 wt. % of water, and
a second container containing an agent (b), wherein the agent (b) comprises:
(b1) water;
(b2) at least one fat component; and
(b3) at least one color-imparting compound.

* * * * *